US009045516B2

(12) United States Patent
Iyer et al.

(10) Patent No.: US 9,045,516 B2
(45) Date of Patent: Jun. 2, 2015

(54) SYNTHETIC LIGANDS FOR THE DIFFERENTIATION OF CLOSELY RELATED TOXINS AND PATHOGENS

(76) Inventors: Suri Saranathan Iyer, Cincinnati, OH (US); Duane Michael Hatch, Nashville, TN (US); Ramesh Ratan Kale, Maharashtra (IN); Alison Ann Weiss, Cincinnati, OH (US); Shantini Dodampe Gamage, Cleves, OH (US); Colleen M. McGannon, Lorain, OH (US)

( * ) Notice: Subject to any disclaimer, the term of this patent is extended or adjusted under 35 U.S.C. 154(b) by 1381 days.

(21) Appl. No.: 12/104,390

(22) Filed: Apr. 16, 2008

(65) Prior Publication Data

US 2009/0042816 A1 Feb. 12, 2009

Related U.S. Application Data

(60) Provisional application No. 60/923,651, filed on Apr. 16, 2007.

(51) Int. Cl.

| | |
|---|---|
| ***G01N 33/00*** | (2006.01) |
| ***C07H 17/02*** | (2006.01) |
| ***C07D 495/04*** | (2006.01) |
| ***G01N 33/569*** | (2006.01) |
| ***G01N 33/68*** | (2006.01) |

(52) U.S. Cl.

CPC .............. *C07H 17/02* (2013.01); *C07D 495/04* (2013.01); *G01N 33/56911* (2013.01); *G01N 33/6893* (2013.01); *G01N 2800/26* (2013.01)

(58) Field of Classification Search

None

See application file for complete search history.

(56) References Cited

U.S. PATENT DOCUMENTS

| | | | |
|---|---|---|---|
| 5,695,759 | A | 12/1997 | Good et al. |
| 5,767,093 | A | 6/1998 | Good et al. |

OTHER PUBLICATIONS

Holmner et al, J. Mol. Biol. 371:754-64, 2007.*

Laugle et al (Abstracts, 39th Regional Meeting of the American Chemical Society, KY, United States, May 20-23, 2007; CRM-057).*

Kale et al (Angew. Chem. Int. Ed. 47:1265-1268 published on line Jan. 2, 2008).*

Laugle et al., Abstracts & Program, May 20-23, 2007, p. 70, Abstract # 57, CERMACS2007—Central Regional Meeting of the American Chemical Society, Northern Kentucky Convention Center, Covington, KY.

Mahajan et al., Abstracts & Program, May 20-23, 2007, p. 180, Abstract # 512, CERMACS2007—Central Regional Meeting of the American Chemical Society, Northern Kentucky Convention Center, Covington, KY.

Kulkarni et al, Carb 2—Synthesis of glycoconjugates for capturing Shiga toxins, Aug. 17-21, 2008, The 236th ACS National Meeting, Philadelphia, PA, [http://oasys2.confex.com/acs/236nm/techprogram/P1206932.HTM].

Hatch et al, Agro 201—Multivalent glycoconjugates for *Escherichia coli* detection, Aug. 17-21, 2008, The 236th ACS National Meeting, Philadelphia, PA, [http://oasys2.confex.com/acs/236nm/techprogram/P1209425.HTM].

Flagler et al, Comparison of Binding Platforms Yields Insights into Receptor Binding Differences between Shiga Toxins 1 and 2, Biochemistry 2010, 49, 1649-1657, c 2010 American Chemical Society, USA.

Hatch. Synthetic Biotinylated Glycoconjugates for the Precise Detection of Toxins and Pathogens, Department of Chemistry, University of Cincinnati, Cincinnati, OH, 45221, USA, Presentation, 235th ACS National Meeting, New Orleans, LA, United States, Apr. 6-10, 2008. American Chemical Society: Washington, D.C.

Hatch, Synthesis of biotinylated bi and tetra antennary glycoconjugates for *E. coli* detection, Department of Chemistry, University of Cincinnati, Cincinnati, OH, 45221, USA, Presentation, 235th ACS National Meeting, New Orleans, LA, United States, Apr. 6-10, 2008. American Chemical Society: Washington, D.C.

Mahajan, Synthesis of Multivalent Ligands for the Detection and Diffrentiation of Shiga Toxins, Department of Chemistry, University of Cincinnati, Cincinnati, OH, 45219, USA, Presentation, 39th Central Regional Meeting of the American Chemical Society, Covington, KY, United States, May 20-23, 2007. American Chemical Society: Washington, D.C.

Laugle et al., Synthesis of Novel Multivalent glycoconjugates for Shiga toxin, Department of Chemistry, University of Cincinnati, Cincinnati, OH, 45251, USA, Poster, 39th Central Regional Meeting of the American Chemical Society, Covington, KY, United States, May 20-23, 2007, CRM-057. American Chemical Society: Washington, D.C.

Siler et al., Synthesis of Divalent and Tetravalent Glycoconjugates for Pathogen Detection, Department of Chemistry, University of Cincinnati, Cincinnati, OH, 45221, USA, Poster, 233rd ACS National Meeting, Chicago, IL, United States, Mar. 25-29, 2007, ORGN-709. American Chemical Society: Washington, D.C.

Jacobson et al, "The Crystal Structure of Shiga Toxin Type 2 with Bound Dissaccharide Guides the Design of a Heterobifunctional Toxin Inhibitor", JBC, Nov. 13, 2013, 289:885-894.

* cited by examiner

*Primary Examiner* — Patricia A Duffy

(74) *Attorney, Agent, or Firm* — Taft Stettinius + Hollister LLP; Adelaide K Leitzel

(57) ABSTRACT

Synthetic ligand compounds and methods of differentiating between Shiga toxin 1 and Shiga toxin 2 are disclosed herein. Another embodiment includes a kit for differentiating between Shiga toxin 1 and Shiga toxin 2. Assay systems and methods for providing an assay are also provided for herein.

13 Claims, 8 Drawing Sheets

Compound A

Compound B

Compound C

I II III IV V VI

R = Ac
R = H

SYNTHETIC LIGANDS FOR THE DIFFERENTIATION OF CLOSELY RELATED TOXINS AND PATHOGENS

REFERENCE TO RELATED APPLICATION

The present application claims priority of U.S. Provisional Application Ser. No. 60/923,651, filed Apr. 16, 2007, the entire disclosure of which is hereby incorporated herein by reference.

TECHNICAL FIELD

Compounds and methods of differentiating between closely related toxins and pathogens and differentiation between serotypes of the same toxin (or pathogen) family. More particularly, synthetic ligands and methods of using such synthetic ligands to differentiate between Shiga toxin 1 and Shiga toxin 2.

BACKGROUND

Multivalent ligands have been shown to capture toxins and pathogens. However, these conventional compounds and techniques have not provided the selectivity necessary to differentiate between closely related toxins or pathogens. Conventional ligands utilized for sensing toxins or pathogens have been full-length antibodies that possess very high specificity and binding affinities. Such antibodies are not ideal as they are not thermally, chemically and biologically stable enough to last for long periods of time. For example, in diagnostic applications for many pathogens, the constant genetic drift renders antibodies ineffective as their specificity and binding affinities decrease over time. Moreover, the presence of antibody matrix effects from a host's immune response can further interfere with detection in clinical samples and again render antibody capture unreliable.

SUMMARY

In accordance with one embodiment, a compound for detecting variant toxins and pathogens, the compound comprising the general formula (I):

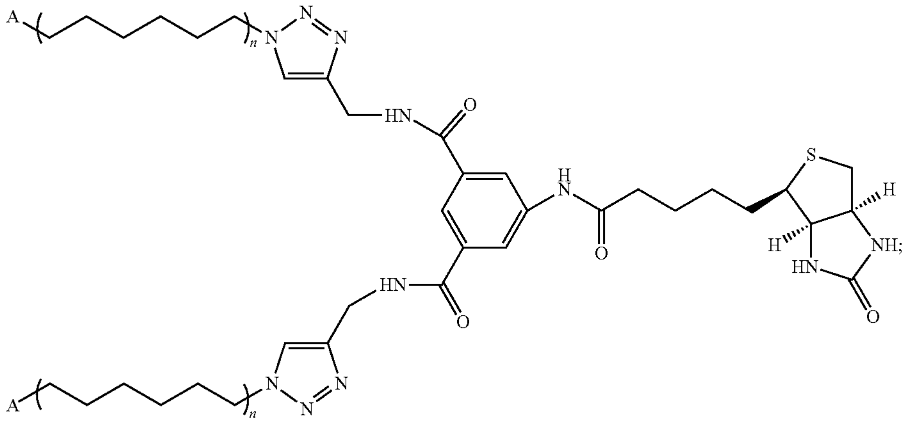

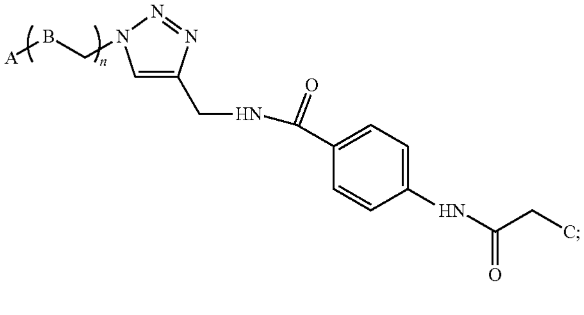

or

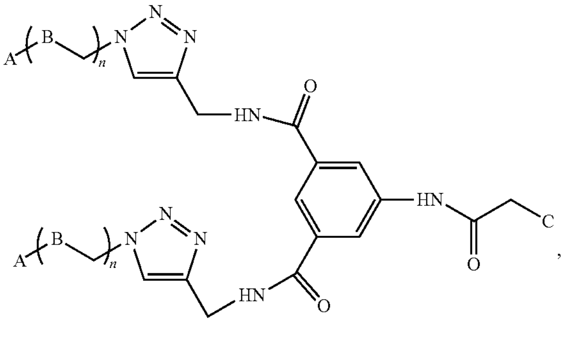

, wherein: n equals 1, 2, 3, 4, 5 or 6; B=O, NH, S, SO, $SO_2$, or P(O)R, C=$NH_2$, COOH, biotin or derivatives thereof, and A comprises a glycoconjugate, wherein the glycoconjugate is selected from the group consisting of:

(a)

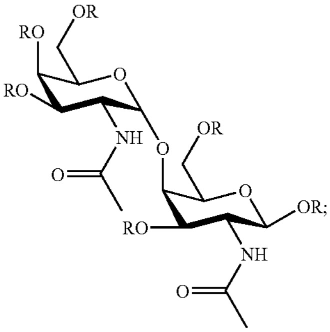

(b)

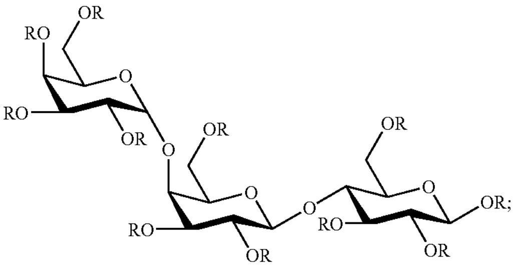

(c)

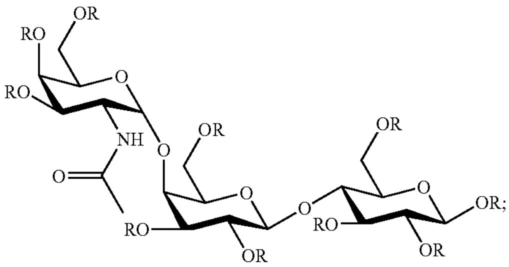

(d)

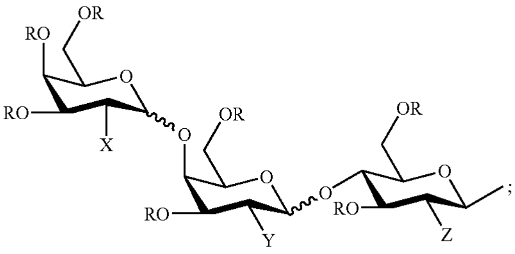

; and (e)

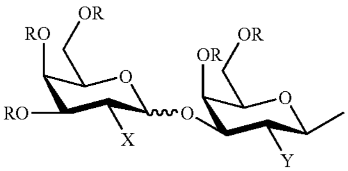

, wherein R comprises H, Ac or derivatives thereof; X=OH, SH, NHAc, $NHCF_3$, $NH_2$, NHCH(=NH)$NH_2$, or derivatives thereof; Y=OH, NHAc, SH, $NHCF_3$, $NH_2$, NHCH(=NH)$NH_2$ or derivatives thereof; Z=OH, NHAc, SH, $NHCF_3$, $NH_2$, NHCH(=NH)$NH_2$ or derivatives thereof.

In accordance with another embodiment, a glycoconjugate consists essentially of:

(a)

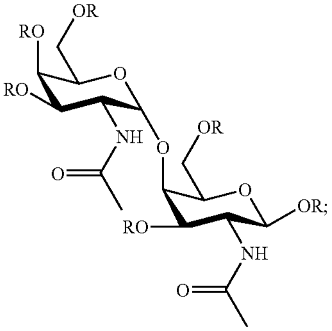

(b)

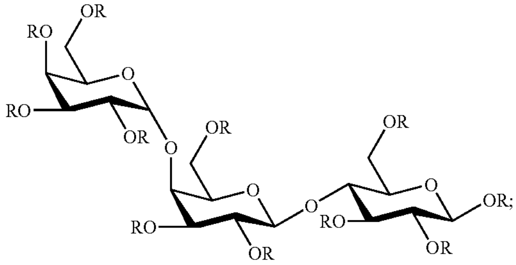

(c)

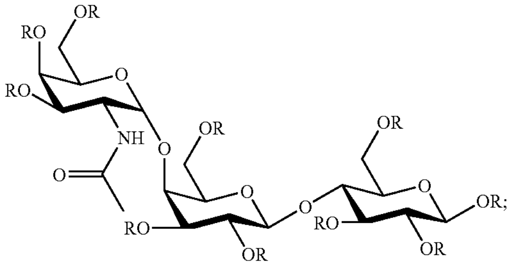

(d)

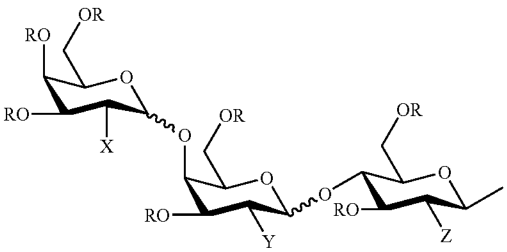

; and

-continued (e)

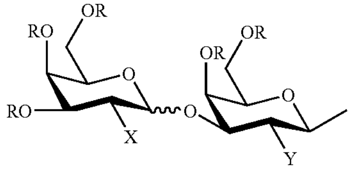, wherein R comprises H, Ac or derivatives thereof; X=OH, SH, NHAc, $NHCF_3$, $NH_2$, NHCH(=NH)$NH_2$ or derivatives thereof; Y=OH, NHAc, SH, $NHCF_3$, $NH_2$, NHCH(=NH)$NH_2$ or derivatives thereof; Z=OH, NHAc, SH, $NHCF_3$, $NH_2$, NHCH(=NH)$NH_2$ or derivatives thereof, and wherein the glycoconjugate has a sufficient affinity to bind to a Shiga toxin for enterotoxigenic *E. coli*, wherein (b) binds with Shiga toxin 1 and (a) and (c) bind with Shiga toxin 2.

In accordance with yet another embodiment, a kit for detecting a toxin comprises at least one container containing at least one capture agent, wherein the at least one capture-agent substantially only binds to Shiga toxin 1 or Shiga toxin 2.

BRIEF DESCRIPTION OF THE DRAWINGS

While the specification concludes with claims particularly pointing out and distinctly claim the invention, it is believed that the same will be better understood from the following description taken in conjunction with the accompanying drawings in which:

DETAILED DESCRIPTION

Figure 1:
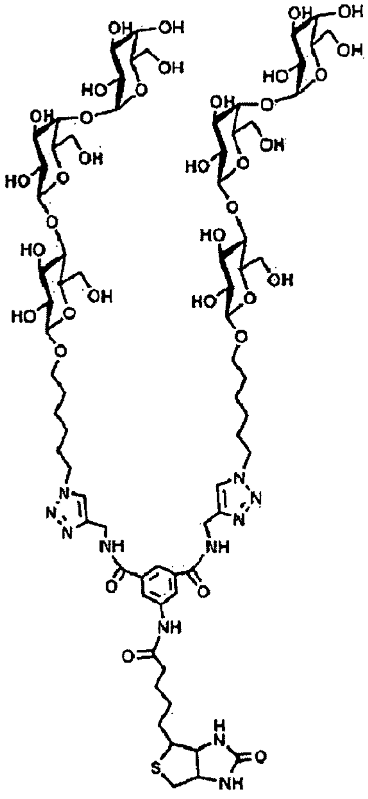
FIG. 1 illustrates three embodiments of synthetic ligands.
Figure 1:
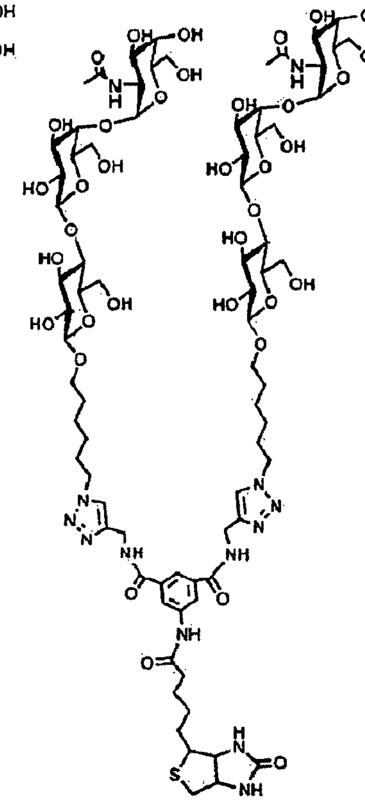
Figure 1:
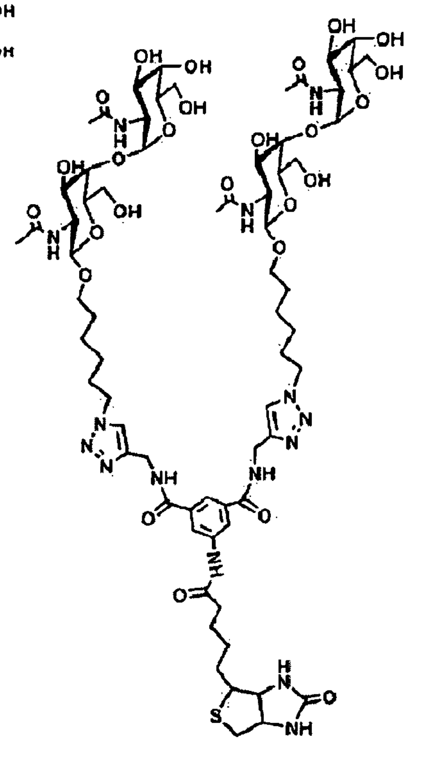

Detection of the Shiga toxin producing *E. coli*, and diagnosis of disease in clinical settings presents a challenge. Isolation of *E. coli* is clinically significant under special circumstances and is dependent on the pathogenic potential of the *E. coli* strains, mainly because some strains produce essentially harmless forms of *E. coli* while other, particularly Shiga toxins, can produce life-threatening diseases (i.e., hemorrhagic colitis and hemolytic uremic syndrome, etc.). Thus, it is important to develop diagnostic tests to detect Shiga toxin to distinguish harmless *E. coli* from isolates that are capable of causing human disease. In addition to detecting the presence of Shiga toxin, it is also important to differentiate between the type of Shiga toxin that is produced. Today, there are two major antigenic groups of Shiga toxins, Shiga toxin 1 (Stx1) and Shiga toxin 2 (Stx2). There are also several minor antigenic variants, Stx2a, Stx2b, Stx2c, Stx2d, Stx2e, for example.

The variants of the Shiga toxins can have very different potencies, particularly related to the impact such toxins have on people. For example, Shiga toxin 2 is more toxic than Shiga toxin 1 for primates. Thus, the development of a compound and method of distinguishing between such variants (such as Stx1 and Stx2) provides a significant advantage in diagnosing and treating the effects of such toxins or pathogens.

Toxins and pathogens (including viruses and bacteria) have been known to bind to cell-surface glycolipids, however, variants of these toxins or pathogens have different binding affinities for closely related glycolipids. These differences in receptor recognition influence which cells will be targeted by the toxin or pathogen and ultimately include the outcome of the potential disease. Such toxins (including their saccharide specificity) include botulinum neurotoxins (gangliosides GD1a, GD1b, GT1a), Ricin (Galactose, N-Acetylgalactose), Shiga toxin 1 (Gal (α1,4) Gal(β1,4)Glc-ceramide or globotriaosylceramide (Gb3)), Shiga toxin 2 (analogues of Gb3, GalNAc (α1,4) Gal(β1,4)Glc-ceramide), Shiga toxin 2e (GalNAc(α1,3) Gal (α1,4) Gal(β1,4)Glc-ceramide (Gb4)), clostridium perfringens epsilon toxin (gangliosides GM1, GM3), staphylococcal enterotoxin B (SEB) Gal (1,4) Gal-ceramide), pertussis toxin (sialic acid, Gal(β1,4)Glc-ceramide, gangliosides), cholera toxin (Ganglioside GM1), *E. coli* enterotoxin, LT-I (Ganglioside GM1), *E. coli* enterotoxin, LT-IIa (Gangliosides GD1b, GD1a, GM1), *E. coli* enterotoxin, LT-IIb (Ganglioside GD1a). The compounds described and claimed herein have been developed to have high selectivity and sensitivity which allow them to bind to specific toxins.

Embodiments are herein described in detail in connection with the drawings of FIGS. 1-11, wherein like numbers indicate the same or corresponding elements throughout the drawings.

The development of synthetic ligands that mimic the natural (or unnatural) receptors associated with the variants for toxins and pathogens has provided for the capacity to differentiate between closely related toxins or pathogens. Examples of some embodiments of such synthetic ligands can be found in FIG. 1. The compounds shown in FIG. 1 include synthetic ligands which are designed to differentiate between closely related toxins. For example, Compound A has been designed to bind to Shiga toxin 1, but not Shiga toxin 2, while Compounds B and C have been designed to bind to Shiga toxin 2, but not Shiga toxin 1. As mentioned herein, having such compounds readily capable of differentiating between variant forms of toxins and pathogens allows for the diagnosis and treatment of any diseases specifically related to theses variant forms of the toxins or pathogens.

Figure 2:
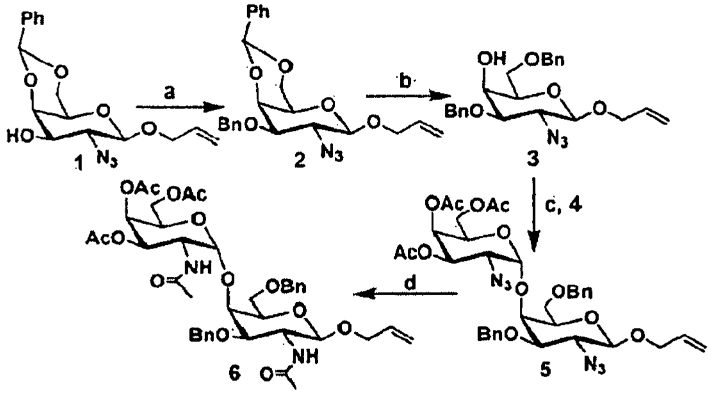
FIG. 2 illustrates the synthesis of a di-N-acetylgalactosamine derivative.

The embodiments of the compounds illustrated in FIG. 1 each include various types of glycoconjugates, which have been configured to bind to variant forms of the Shiga toxin. It will be understood that these glycoconjugates can be produced using various process methods, however, for purposes of illustration, one embodied method for the synthesis of a di-N-acetylgalactosamine derivative (i.e., allyl (2-N-acetamido-2-deoxy-3,4,6 tri-O-acetyl α-D-galactopyranosyl)-(1→4) 2-N-acetamido-2-deoxy-3,6 di-O-benzyl-β-D-galactopyranoside) is illustrated in FIG. 2 and discussed herein. The synthesis of the di-N-acetyl galactosamine was generally achieved by coupling an acceptor obtained by a 2-step procedure from allyl-e-deoxy-2-azido-4,6-benzylidene-β-D-galactopyranoside, with trichloroacetimidate donor in the presence of catalytic amount of TMSOTf yielding the disaccharide form of the di-N-acetylated galactose derivative.

Figure 3:
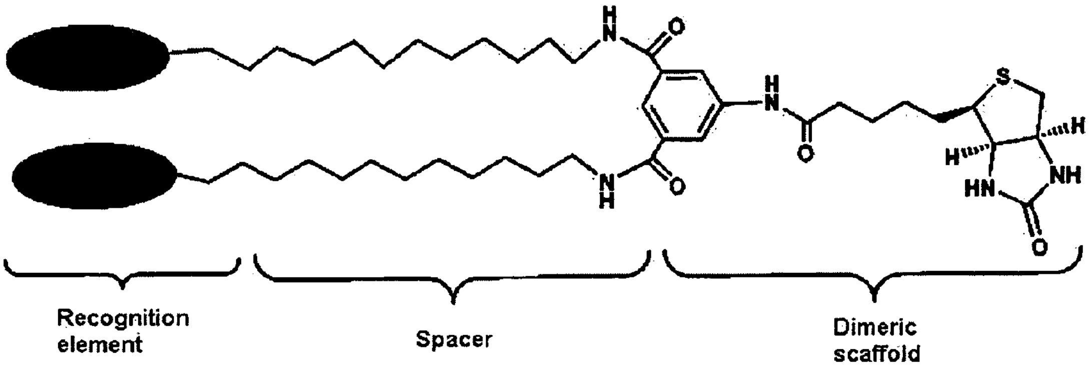
FIG. 3 generally represents a compound arrangement for a high affinity multivalent ligand.

The synthetic ligands which are discussed herein generally have three components which include a recognition element, spacer (which can be terminated in an azide) and a dimeric scaffold bearing two alkynes all of which are generally represented by the embodiment illustrated in FIG. 3. The embodiment of the ligand represented in FIG. 3 has two recognition elements. The recognition elements are adapted to bind to toxins and pathogens and can include antibodies, antibody fragments, aptamers, carbohydrates, peptides DNA or RNA. Moreover, the two recognition elements represented in FIG. 3 can be the same or different. The spacer illustrated in FIG. 3 can vary in length and can be a factor in increasing the selectivity or; affinity the synthetic ligand has for a particular toxin or pathogen. The embodiment of the scaffold shown in FIG. 3 is a multivalent dimeric scaffold. The dimeric scaffold affords easy access to multivalency by virtue of one tetramer binding to four biotins.

The following examples provide three different embodiments directed to the synthesis of the three compounds shown in FIG. 1.

EXAMPLE 1

Synthesis of Compound C

Figure 4:
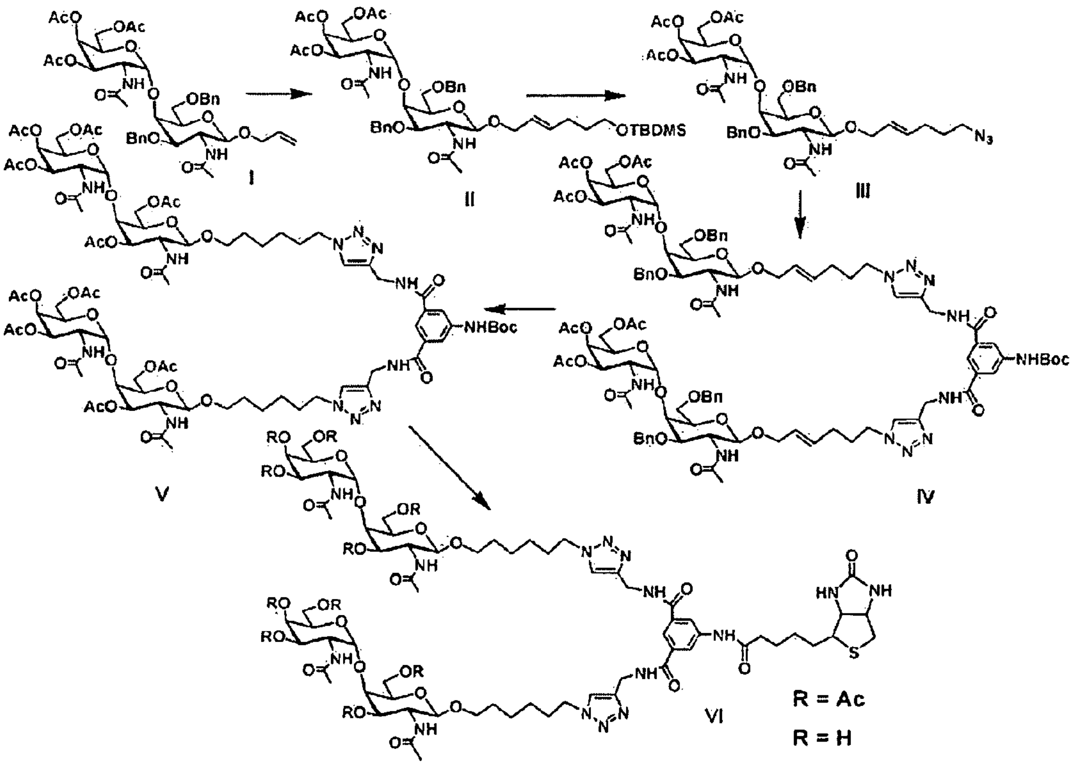
FIG. 4 illustrates stepwise formation of a synthetic ligand.

A synthesis of Compound C is illustrated in FIG. 4. The di-N-acetylated galactose derivative as shown in FIG. 2 can be processed to form the embodied synthetic ligand compound (VI) illustrated in FIG. 4. The process of synthesizing compound (VI) as shown in FIG. 4 includes having the di-N-acetylated galactose derivative (I) (i.e., Allyl (2-N-acetamido-2-deoxy-3,4,6 tri-O-acetyl α-D-galactopyranosyl)-(1→4) 2-N-acetamido-2-deoxy-3,6 di-O-benzyl-β-D-galactopyranoside) modified so that the azide functionalities were reduced to the N-acetyl groups using thiolacetic acid.

Compound (I) (116 mg, 0.15 mmol) and (1,1-Dimethylethyl)dimethyl(4-pentenyloxy)silane (300 mg, 1.5 mmol) were dissolved in 15 ml $CH_2Cl_2$ and benzylidene-bis(tricyclohexylphosphine)dichlororuthenium (Grubb's 1st generation catalyst, 28 mg, 0.034 mmol) was added to it under argon atmosphere. The resulting orange colored solution was refluxed for 16 h. The reaction mixture was then cooled to room temperature, the solvent was removed in vacuo and the crude product was purified by flash column chromatography, eluting with a 80:20 mixture of EtOAc:hexane, to give Compound (II) (i.e., 6-[(1,1-Dimethylethyl)dimethylsilyl]oxy]-2-en (2-N-acetamido-2-deoxy-3,4,6 tri-O-acetyl-α-D-galacto-pyranosyl)-(1→4)-2-N-acetamido-2-deoxy-3,6 di-O-benzyl-O-D galacto pyranoside) as a white solid (123 mg, 87%). HRMS: Calculated for $[C_{48}H_{70}N_2O_{15}Si+H]^+$: 943.4619. Found 943.4666.

Compound (II) (100 mg, 0.032 mmol) was dissolved in THF (2 ml) and cooled to 0° C. A solution of TBAF in THF (0.2 ml of 1 M solution in THF, 0.127 mmol) was added drop wise and the resulting solution was stirred for 3 h at room temperature. The reaction was quenched using saturated $NaHCO_3$ solution and the product was extracted with 2×25 ml EtOAc. The organic layer was collected, dried over anhydrous $Na_2SO_4$, filtered and the solvent was removed in vacuo. The crude product was purified by flash column chromatography, eluting with a 10:90 mixture of MeOH and EtOAc, to give the alcohol as a white solid (76 mg, 86.9%). HRMS Calculated for $[C_{42}H_{56}N_2O_{15}Na]^+$851.3578. Found 851.3595. Next, the alcohol (90 mg, 0.109 mmol) and diisopropyl ethyl amine (0.270 ml, 0.155 mmol) were dissolve 4 in $CH_2Cl_2$ (15 ml) and cooled to −10° C. Methane sulfonyl chloride (0.1 ml, 129 mmol) was added drop wise and the resulting solution was stirred for 1 h slowly warming to room temperature and further stirred at room temperature for 4 h. Water was added to the solution and the product was extracted with 2×25 ml $CH_2Cl_2$. The organic layer was collected, dried over anhydrous $Na_2SO_4$ and the solvent was removed in vacuo to give mesylated product which was used in next reaction without purification. The mesylated intermediate and sodium azide (100 mg, 1.53 mmol) were dissolved in 3 ml of DMF and the resulting solution was stirred at 65° C. for 5 h. The reaction mixture was then cooled to room temperature and the product was extracted with 2×25 ml EtOAc. The organic layer was collected, dried over anhydrous $Na_2SO_4$, filtered and the solvent was removed in vacuo and the crude product was purified by flash column chromatography, eluting with 100% EtOAc, to give Compound (III) (i.e., 6-Azido-2-en (2-N-acetamido-2-deoxy-3,4,6 tri-O-acetyl-α-D-galacto pyranosyl)-(1→4)-2-N-acetamido-2-deoxy-3,6-di-O-benzyl-β-D-galactopyranoside) as a white solid (62 mg, 68.9% over 3 steps). HRMS Calculated for $[C_{42}H_{55}N_5O_{14}Na]^+$: 876.3643. Found: 876.3663.

Compound (III) (10 mg, 0.028 mmol), Compound (II) (54 mg, 0.063 mmol), sodium ascorbate (14 mg, 0.071 mmol), and $CuSO_4$ (9 mg, 0.036 mmol) were mixed in a 1:1 mixture of water and THF (3 ml) was stirred at room temperature for 24 h. After evaporation of the solvents, the crude product was directly loaded onto a silica gel column and the product was purified by flash column chromatography, eluting with 85:15 mixture of EtOAc and $CH_3OH$ (methanol), to give Compound (IV) as a white solid (50 mg, 86%). HRMS Calculated for $[C_{103}H_{131}N_{13}O_{32}+2H]^{2+}$: 1031.9584 Found: 1031.9696.

Compound (IV) (45 mg, 0.022 mmol) was dissolved in $CH_3OH$ (10 ml) and $Pd(OH)_2$ on carbon (30 mg) was added to it. The reaction mixture was stirred under hydrogen atmosphere under 1 atm pressure and at room temperature for 12 h. The catalyst was filtered through celite and the solvent was removed under vacuo to yield the debenzylated intermediate. The tetrahydroxide was dissolved in 3 ml of dry pyridine; catalytic amount of DMAP (5 mg) was added to it and cooled to 0° C. Acetic anhydride (1.5 ml) was then added to it at 0° C. After stirring overnight, the solvent was removed in vacuo and the residue was subjected to column chromatography, eluting with to give Compound (V) as a white solid (36 mg, 88%). HRMS Calculated for $[C_{83}H_{119}N_{13}O_{36}+2H]^{2+}$: 937.9013 Found: 937.9031.

Compound (V) (10 mg, 5.33 mmol) was taken in dry $CH_2Cl_2$ (2 ml) and TIPS (0.020 ml) was added to it via syringe. TFA (0.100 ml) was added drop wise and stirred at room temperature for 12 h. Saturated $NaHCO_3$ solution was used to quench the reaction and the compound was extracted in 2×25 ml $CH_2Cl_2$. The organic layer was dried over anhydrous $Na_2SO_4$ and the solvent was removed in vacuo. The crude product was purified by flash column chromatography, eluting with a 1:4 mixture of hexane and EtOAc, to give the free amine as a white solid. This product was used without further purification in the next step. CDMT (2 mg, 0.011 mmol) was dissolved in dry THF (0.5 ml) cooled to 0° C. and NMM (0.010 ml) was added to it and stirred for 30 min at 0° C. Biotin (2.2 mg, 0.009 mmol) in DMF (0.5 ml) was added dropwise to the mixture and the mixture was reacted overnight at 0° C. under continuous stirring. The amine (8 mg, 0.0045 mmol) and NMM (0.010 ml) in DMF:THF (0.5 ml, 1:1) were added dropwise to the mixture under stirring at 0° C. The mixture was reacted for 20 h slowly warming to room temperature. Water was added drop wise to the mixture while stirring and the compound extracted in 2×25 ml of EtOAc. The organic layers were dried over anhydrous $Na_2SO_4$, filter and solvent removed in vacuo. The residue was purified by column chromatography, eluting with a 1:9 mixture of methanol and EtOAc, to give Compound (VI) as a white solid (5.5 mg, 61%). HRMS Calculated for $[C_{88}H_{125}N_{15}O_{36}S+2H]^{2}+$: 1000.9139. Found 1000.9156.

Compound (VI) (4 mg, 0.002 mmol) was dissolved in $CH_3OH$ (2 ml) and a solution of NaOMe in $CH_3OH$ (0.7 M, 0.5 ml) was added and the reaction mixture was stirred at room temperature for 16 h. The reaction was neutralized by careful addition of Amberlite-15H' resin and the resin was filtered. The solvent was removed in vacuo and the residue was purified by Biogel P-2 gel column chromatography, using water as eluent. The product was lyophilized to give Compound C, where R═H, as a white solid (2.7 mg, 86%). HRMS Calculated for $[C_{68}H_{105}N_{15}O_{26}S+2H]^{2+}$: 790.8612. Found 790.8580.

EXAMPLE 2

Synthesis of Compound B

Figure 5:
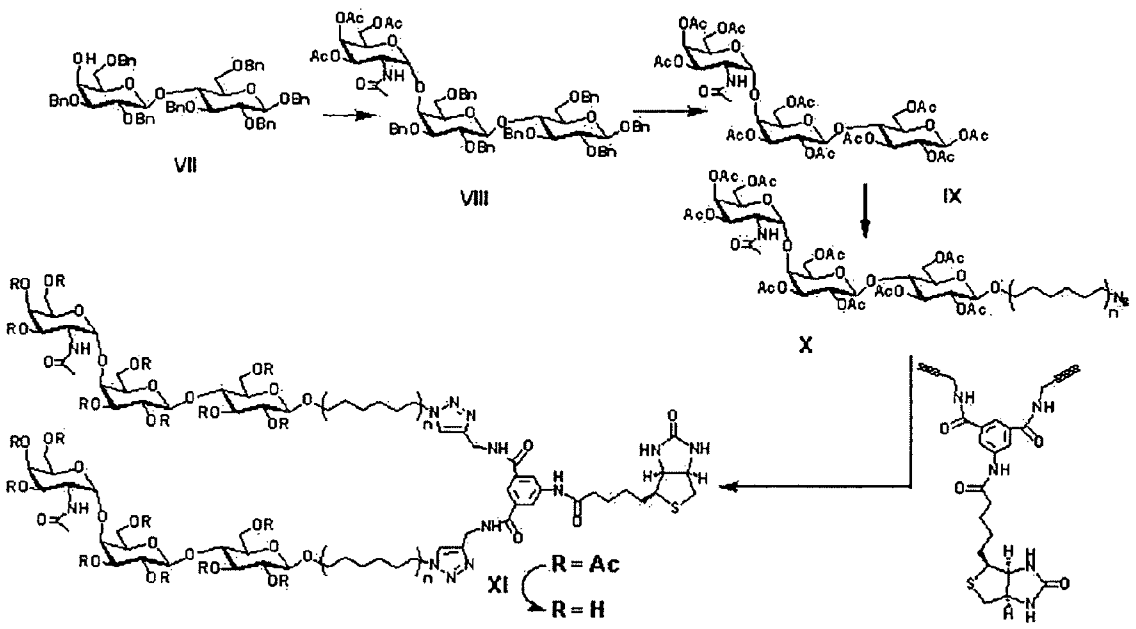
FIG. 5 illustrates another stepwise formation of a synthetic ligand.

A synthesis of Compound B is illustrated in FIG. 5. Compound (VIII) is formed from a trichloroacetimidate (210 mg, 0.22 mmol) and an acceptor (Compound (VII) (120 mg, 0.26 mmol) were dissolved in $CH_2Cl_2$ (15 ml) and cooled, to −20° C. TMSOTf (0.093 ml of a 0.22 M solution in $CH_2Cl_2$, 0.022 mmol) was added dropwise via syringe and the resulting solution was stirred for 1.5 h at −20° C. Upon completion (by TLC), the reaction was quenched using cold saturated $NaHCO_3$ solution and the product was extracted with 2×25 ml $CH_2Cl_2$. The organic layer was collected, dried over anhydrous $Na_2SO_4$, and the solvent was removed in vacuo. The crude product was purified by flash column chromatography, eluting with a 1:1 mixture of hexane and EtOAc, to give the coupled product as a white solid (194 mg, 60.0%). HRMS Calculated for $[C_{73}H_{79}N_3O_{18}+Na]^+$1308.5256. Found: 1308.5281. This white solid was dissolved in thioacetic acid (1.5 ml) and the resulting solution was stirred for 48 h at room temperature. The solvent was removed in vacuo and the crude product was purified by flash column chromatography, eluting with 100% EtOAc, to give Compound (VIII) (i.e., Benzyl (2-N-acetamido 2-deoxy 3,4,6-tri-O-acetyl-α-D-galacto pyranosyl) (1→4) (2,3,6-tri-O-benzyl-β-D-galactopyranosyl)(1→4) 2,3,6-tri-O-benzyl-β-D-glucopyranoside) as a white solid (105 mg, 53.5%). HRMS Calculated for $[C_{75}H_{83}NO_{19}+Na]^+$1324.5457. Found: 1324.5483.

Compound (VIII) (105 mg, 0.081 mmol) was dissolved in $CH_3OH$ (10 ml) and $Pd(OH)_2$ on carbon (30 mg) was added to it and the reaction mixture was stirred under 1 atm hydrogen atmosphere at room temperature for 12 h. The catalyst was filtered using celite and the solvent was removed under vacuo to yield the debenzylated product as a white solid. The solid material was dissolved in 8 ml of dry pyridine, catalytic amount of DMAP (5 mg) was added to it and cooled to 0° C. Acetic anhydride (2.5 ml) was added to it and stirred overnight. The solvent was removed in vacuo and the residue was subjected to column chromatography, eluting with 100% EtOAc to give Compound (IX) (i.e., Acetyl (2-N-acetamido 2-deoxy 3,4,6-tri-O-acetyl-β-D-galacto pyranosyl) (1→4) (2,3,6-tri-O-acetyl-β-D-galactopyranosyl)(1-4) 2,3,6-tri-O-benzyl-β-D-glucopyranoside) as a white solid (63 mg, 81.5% over 2 steps). HRMS Calculated for $[C_{40}H_{55}NO_{26}+Na]^+$ 988.2910. Found: 988.2965.

Compound (IX) 130 mg, 0.135 mmol) was dissolved in 3 ml of anhydrous THF and $NH_2NH_2$.HOAc (15 mg, 0.162 mmol) was added to it. The reaction was stirred at room temperature for 6 h. The reaction mixture was diluted with 5 ml of EtOAc and 5 ml of water was added the organic layer was separated and dried in vacuo to give the hemiacetal (105 mg, 85%), which was directly used in the next step. Anhydrous $K_2CO_3$ (400 mg, 2.89 mol) was added to the solution of hemiacetal 120 mg, 0.129 mmol) and trichloroacetonitrile (100 μL, 1.0 mmol) in $CH_2Cl_2$ (3 ml) at room temperature. The reaction mixture was stirred at room temperature for 8 h, washed with water and the organic layer was dried over anhydrous $Na_2SO_4$, filtered and concentrated in vacuo. The residue was purified by column chromatography, eluting with EtOAc, to give the trichloroimidate as a pale yellow solid (121 mg, 87%). The imidate (64 mg, 0.060 mmol) and 1-azido hexanol (17 mg, 0.12 mmol) were dissolved in $CH_2Cl_2$ (2 ml) and cooled to 0° C. A 0.22 M solution of TMSOTf in $CH_2Cl_2$ (0.055 ml, 0.012 mmol, 0.2 eq.) was added drop wise and the resulting solution was stirred for 1.5 h at 0° C. The reaction was quenched by saturated $NaHCO_3$ solution (cold) and extracted with $CH_2Cl_2$. The organic layer was dried over anhydrous sodium sulfate, filtered, concentrated in vacuo and purified by column chromatography, eluting with EtOAc to give Compound (X) (i.e., 1-Azido-hexyl (2-N-acetamido 2-deoxy 3,4,6-tri-O-acetyl-α-D-galacto pyranosyl) (1→4) (2,3,6-tri-O-acetyl-β-D-galactopyranosyl) (1→4) 2,3,6-tri-O-acetyl-β-D-gluco pyranoside) as a syrupy solid (28 mg, 46%). HRMS Calculated for $[C_{44}H_{64}N_4O_{25}+Na]^+$: 1071.3764. Found: 1071.3786.

Compound (X) (14 mg, 0.0137 mmol), a biotin (3 mg, 0.0062 mmol), sodium ascorbate, (3 mg, 0.015 mmol), and $CuSO_4$ (1.9 mg, 0.008 mmol) were mixed in a 1:1 mixture of water and THF (2 ml) was stirred at room temperature for 24 h. After evaporation of the solvents, the crude product was directly loaded onto a silica gel column and the product was purified by flash column chromatography, eluting with a 9:1 mixture of $CH_2Cl_2$ and $CH_3OH$, to give Compound (XI) as a white solid (12 mg, 75%). HRMS Calculated for $[C_{112}H_5N_{13}O_{54}S+2Na]^{2+}$: 1312.4677. Found 1312.4660. Compound (XI) (6 mg, 0.0023 mmol) was dissolved in $CH_3OH$ (1 ml) and a solution of NaOMe in $CH_3OH$ (0.7 M, p. 5 ml) was added. The reaction mixture was stirred at room temperature for 16 h. The reaction was neutralized by careful addition of Amberlite-15 $H^+$ resin and the resin was filtered. The solvent was removed in vacuo and the residue was purified by Biogel P-2 gel column chromatography, using water as eluent. The product was lyophilized to give Compound B, where R═H, as a white solid (3.7 mg, 87%). HRMS Calculated for $[C_{76}H_{119}N_{13}O_{36}S+2H]^{2+}$: 911.8873. Found: 911.8820.

EXAMPLE 3

Synthesis of Compound A

Figure 6:
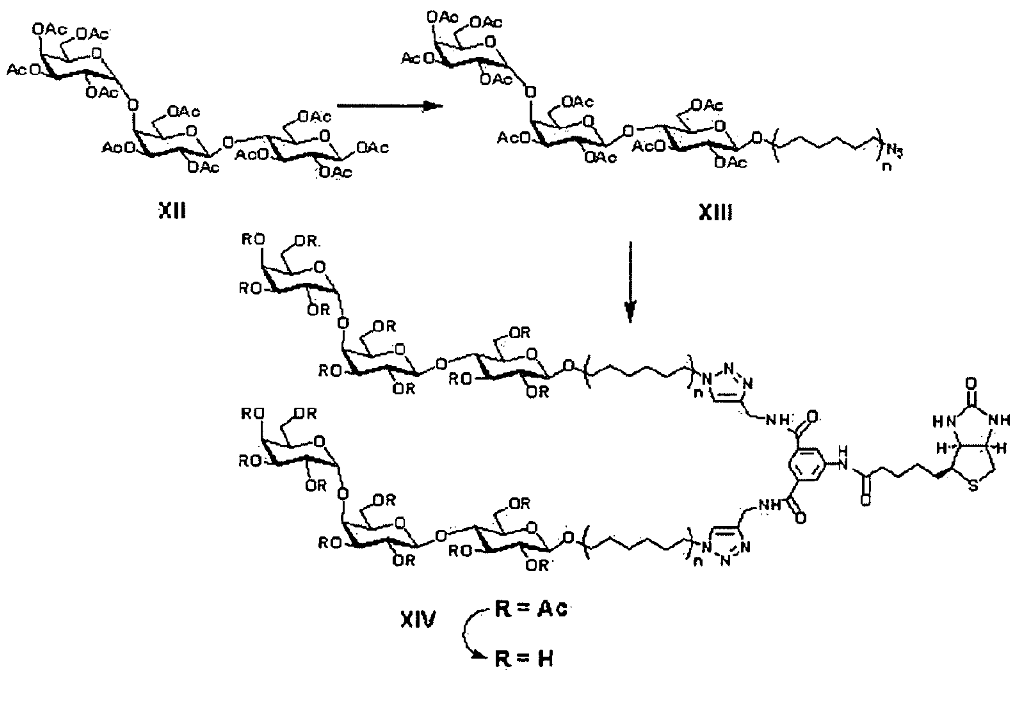
FIG. 6 illustrates another stepwise formation of a synthetic ligand.

A synthesis of Compound A is illustrated in FIG. 6. Compound (XIII) is formed when Compound (XII) (i.e., Acetyl (2,3,4,6-tetra-O-acetyl-β-D-galactopyranosyl)(1-4) (2,3,6-tri-O-acetyl-β-D-galactopyranosyl)(1→4) 2,3,6-tri-O-acetyl-α,β-D-glucopyranoside) (96 mg, 0.099 mmol) was dissolved in 3 ml of dry THF and $NH_2NH_2$.HOAc (11 mg, 0.119 mmol) was added to it. The reaction was stirred at room temperature for 6 h. The reaction mixture was diluted with 5 ml of EtOAc and 5 ml of water was added the organic layer was separated and dried in vacuo to give the hemiacetal (75 mg, 91%), which was directly used in the next step. Anhydrous $K_2CO_3$ (106 mg, 0.76 mol) was added to the solution of hemiacetal (70 mg, 0.076 mmol) and trichloroacetonitrile (77 μL, 0.76 m mol) in $CH_2Cl_2$ (3 ml) at room temperature. The reaction mixture was stirred at room temperature for 16 h, washed with water, and the organic layer was dried over anhydrous $Na_2SO_4$, filtered and concentrated in vacuo. The residue was purified by column chromatography, eluting with a 1:1 mixture of hexane and EtOAc, to give the trichloroimidate as a pale yellow solid (72 mg, 88%). The imidate (70 mg, 0.065 mmol) and 1-azido hexanol (19 mg, 0.13 mmol) were dissolved in $CH_2Cl_2$ (2 ml) and cooled to 0° C.). A 0.22 M solution of TMSOTf in $CH_2Cl_2$ (0.13 mmol, 0.2 eq.) was added drop wise and the resulting solution was stirred for 1.5 h at 0° C. The reaction was quenched by saturated $NaHCO_3$ solution (cold) and extracted with $CH_2Cl_2$. The organic layer was dried over anhydrous sodium sulfate, filtered, concentrated in vacuo and purified by column chromatography, eluting with a 3:7 mixture of hexane and EtOAc, to give Compound (XIII) (i.e., 1-Azido-hexyl(2,3,4,6-tetra-O-acetyl-α-D-galactopyranosyl) (1-4) (2,3,6-tri-O-acetyl-β-D-galactopyranosyl) (1→4) 2,3,6-tri-O-acetyl-β-D-glucopyranoside) as a solid (38 mg, 68%). HRMS Calculated for $[C_{44}H_{63}N_3O_{26}+Na]^+$: 1072.3592. Found: 1072.3586.

Compound (XIII) (19 mg, 0.0183 mmol), a biotin (4 mg, 0.0083 mmol), sodium ascorbate 6 mg, 0.030 mmol), and $CuSO_4$ (4 mg, 0.014 mmol) were mixed in a 1:1 mixture of water and THF (2 ml) was stirred at room temperature for 24 h. After evaporation of the solvents, the crude product was directly loaded onto a silica gel column and the product was purified by flash column chromatography, eluting with a 8.5: 15 mixture of $CH_2Cl_2$ and $CH_3OH$, to give Compound (XIV) as a white solid (14 mg, 67%). HRMS Calculated for $[C_{112}H_{153}N_{11}O_{56}S+2H]^{2+}$: 1290.9664. Found 1290.9673. Compound (XIV) (6 mg, 0.0023 mmol) was dissolved in $CH_3OH$ (1 ml and a solution of NaOMe in $CH_3OH$ (0.7 M, 0.5 ml) was added. The reaction mixture was stirred at room temperature, for 16 h. The reaction was neutralized by careful addition of Amberlite-15 $H^+$ resin and the resin was filtered. The solvent was removed in vacuo and the residue was purified by Biogel P-2 gel column chromatography, using water as eluent. The product was lyophilized to give Compound A, where R═H, as a white, solid (3.4 mg, 84%). HRMS Calculated for $[C_{72}H_{113}N_{11}O_{36}S+2H]^{2+}$: 870.8608. Found: 870.8644.

Figure 7:
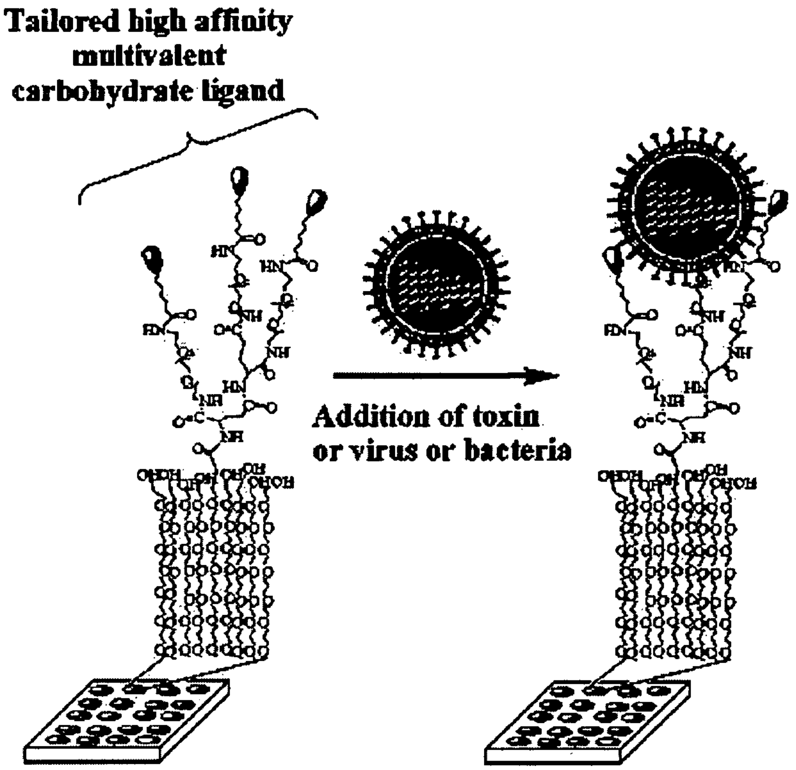
FIG. 7 generally depicts an assay for detection of a toxin using a synthetic ligand.
Figure 8A:
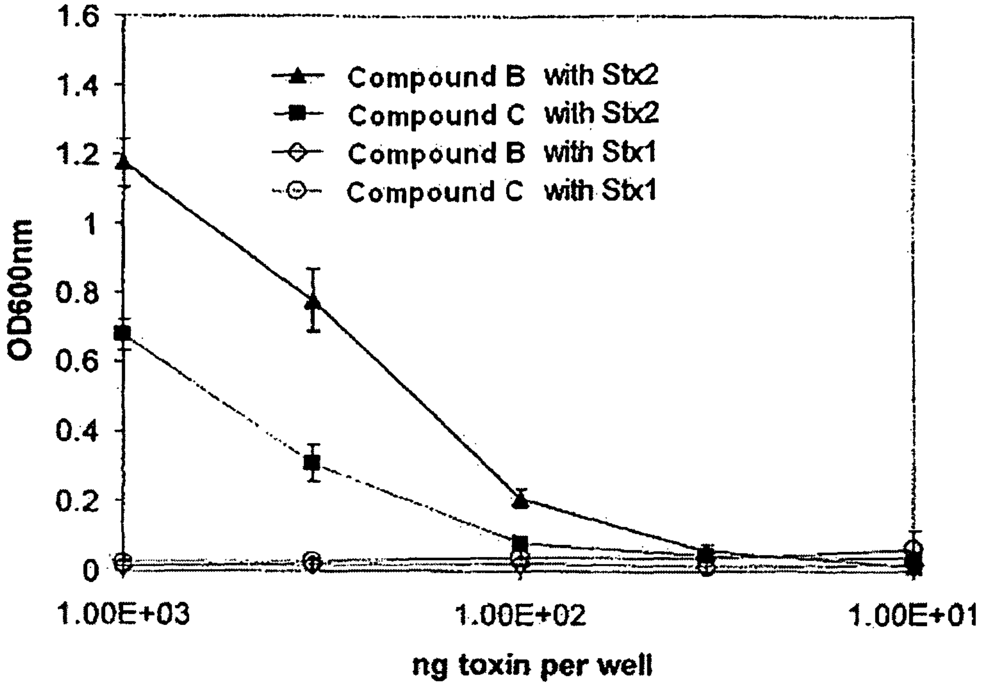
FIG. 8*a* represents a line graph illustrating the binding relationship between Compound B and C with the variants of enterotoxigenic *E. coli*, Shiga toxin 1 or Shiga toxin 2.

As noted herein, synthetic ligands, like the three embodiments of synthetic ligands described above, can be used to differentiate between variant Shiga toxins (i.e., Shiga toxin 1 and Shiga toxin 2). To determine the selectivity and binding affinities of synthetic ligands for any particular variant of the toxin, various detection assay formats and transducers can be utilized. For example, transducers such as mass loading devices (i.e., surface acoustic wave, microcantilevers, surface plasmon resonance, interferometric methods), optical devices, and electrochemical devices can be used. Possible assay formats include single binding events as used in mass loading device or sandwich assays as used in optical sensors or conventional microbiology assays (i.e., ELISA), luminescence based assay, fluorescence based assay, dipstick assays, or nanoparticles can be used. In one embodiment, an ELISA analysis was performed on one of the three embodiments of synthetic ligands described above. In one particular embodiment, the ELISA procedure included having the synthetic ligand diluted in either PBS or water and added to pre-coated microwell plates or containers. In another embodiment, these wells can be pre-coated (or treated) with streptavidin. In this embodiment, the synthetic ligands were then exposed to an environment having the Shiga toxin for a sufficient period of time (for example, 2 hours at room temperature). Finally, in this embodiment, a color was associated with the tested samples against a control and analyzed by evaluating the absorbance of the samples using an ELX800 microplate reader. A general representation showing a toxin attached to the synthetic ligand contained in a well of the assay is shown in FIG. 7. The results of the ELISA procedure are provided in FIGS. 8*a* and 8*b*, which illustrate the amount of toxin present per well containing a particular synthetic ligand. As shown in FIG. 8*a*, the N-acetyl substituted galactosamine for Compounds B and C substantially bound to the Shiga toxin 2 (serotype (O1117 LPS), while the Shiga toxin 1 failed to effectively bind to either compound. In fact, the glycoconjugates associated with Compound B had a greater affinity to bind to Shiga toxin 2 than did those associated with Compound C. In contrast, FIG. 8*b* illustrates that Compound A substantially bound with Shiga toxin 1, but did not effectively bind with Shiga toxin 2.

Figure 8B:
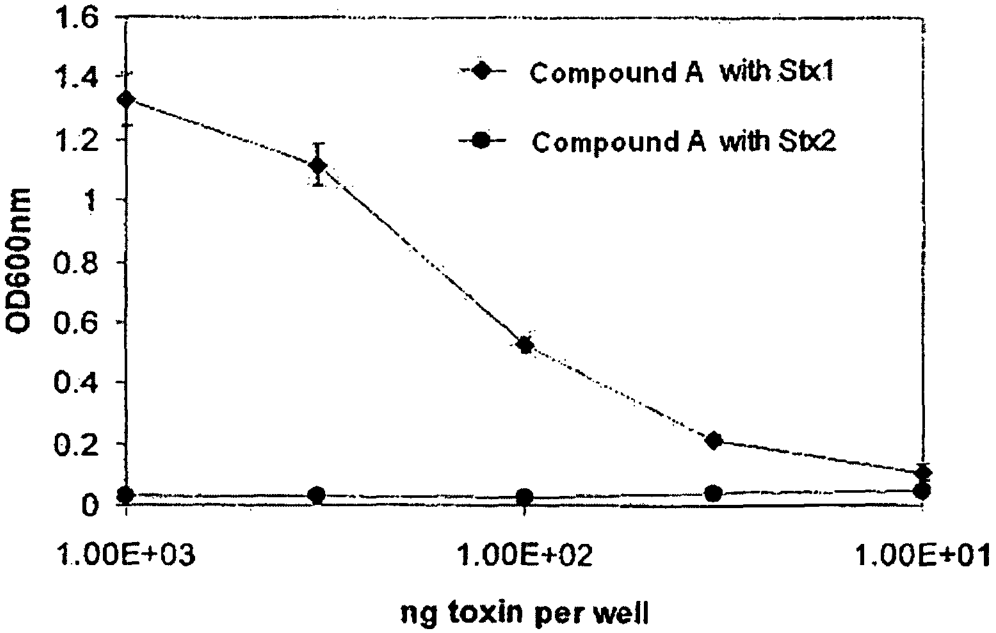
FIG. 8*b* represents a line, graph illustrating the binding relationship between Compound A with the variants of enterotoxigenic *E. coli*, Shiga toxin 1 or Shiga toxin 2.

The results shown in FIGS. 8*a* and 8*b* further support that synthetic ligands can be used to differentiate between Shiga toxin 1 and Shiga toxin 2. In fact, the results illustrated in FIGS. 8*a* and 8*b* indicate that the N-acetyl groups at the second position for Compounds B and C provide the location for the binding with the toxin which is substantially exclusively with Shiga toxin 2. Moreover, it is important to note that the embodiments of the synthetic ligands tested and discussed above had such high binding-capacities that the results indicated the toxins being bound in nanogram quantities from impure culture solutions. Because real world use of such samples and testing procedures are often times not clean, the binding capacity of these ligands is significant, particularly due to the small quantity of the toxin which can be detected and identified. Thus, the three embodied synthetic ligands discussed above as well as other contemplated and embodied ligands, could be used in hand-held and environmental biosensors used in the field. Such synthetic ligands can be used in these environments because they are stable at ambient temperatures and for long periods of time. The synthetic ligands provide high levels of selectivity and sensitivity which can be utilized in diagnostic kits to detect variant forms of the Shiga toxin. One embodiment of such a kit could include at least one container containing at least once capture agent (i.e., synthetic ligand) which selectively binds to only Shiga toxin 1 or Shiga toxin 2. Such kits could include multiple containers containing different capture agents, or an embodiment could include each kit designated to include a specific capture agent.

Figure 9A:
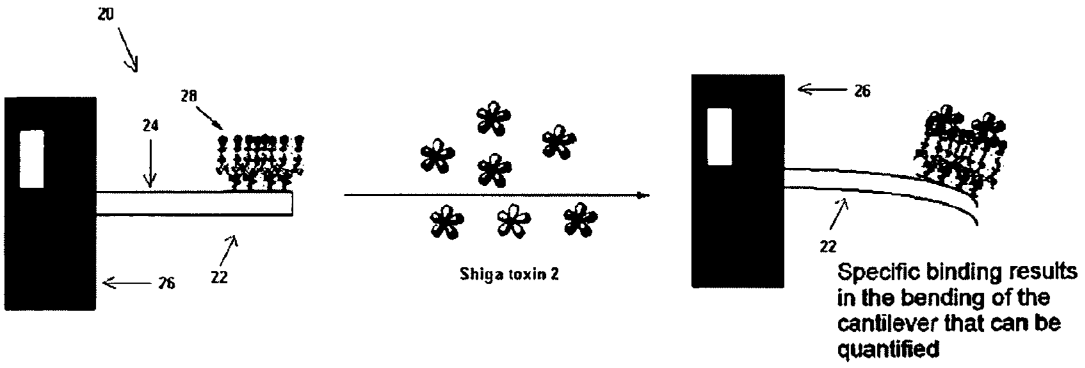
FIG. 9*a* illustrates a biological assay system for detecting the presence of a particular toxic substance.
Figure 9B:
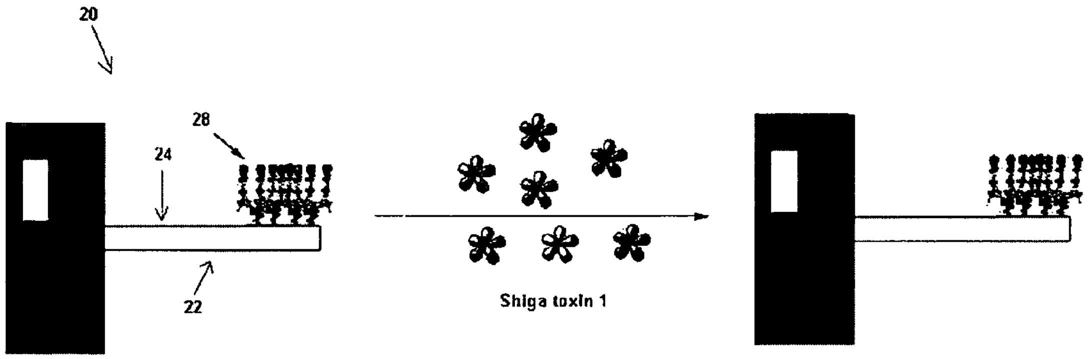
FIG. 9*b* illustrates a biological assay system for detecting the presence of a particular toxic substance.

Another embodiment for a diagnostic kit is illustrated in FIGS. 9*a* and 9*b*. As shown in this embodiment, the kit 20 includes a base layer 22 (i.e., polyolefin flexible film) having a surface 24 which extends from an attached structure 26. The synthetic ligands 28 can be attached to the surface 24 of the base layer 22. In one embodiment, the surface 24 of the base layer 22 is treated with a coating to assist in immobilizing the synthetic ligand 28. As shown in FIG. 9*a*, the synthetic ligand 28 (in this example assume Compound B) is exposed to Shiga toxin 2. The synthetic ligand 28 binds to the Shiga 2 toxin which increases the amount of material on the base layer 22 which is cantilevered relative to the attached structure 26, thus causing the base layer 22 to bend. This bending can be quantified and measured providing an indication to the user that the sample being tested is positive for the Shiga toxin 2. In contrast, as illustrated in FIG. 9*b*, using the same embodied synthetic ligand 28 (i.e., Compound B) as in FIG. 9*a*, but instead exposing the synthetic ligand 28 to an environment with only Shiga toxin 1, finds that the synthetic ligand 28 does not bind to this variant of the toxin and thus the base layer 22 does not bend. It is contemplated that a variety of methods and systems could be used to measure and detect the presence or absence of a variant of the Shiga toxin when using the synthetic ligands described in claimed herein.

The use of synthetic ligands to detect and quantify the presence or absence of variants of the Shiga toxin is a significant advancement. As shown, the examples provided indicate that food products can be analyzed and tested for the variants in the Shiga toxin using synthetic ligands.

EXAMPLE A

Figure 10A:
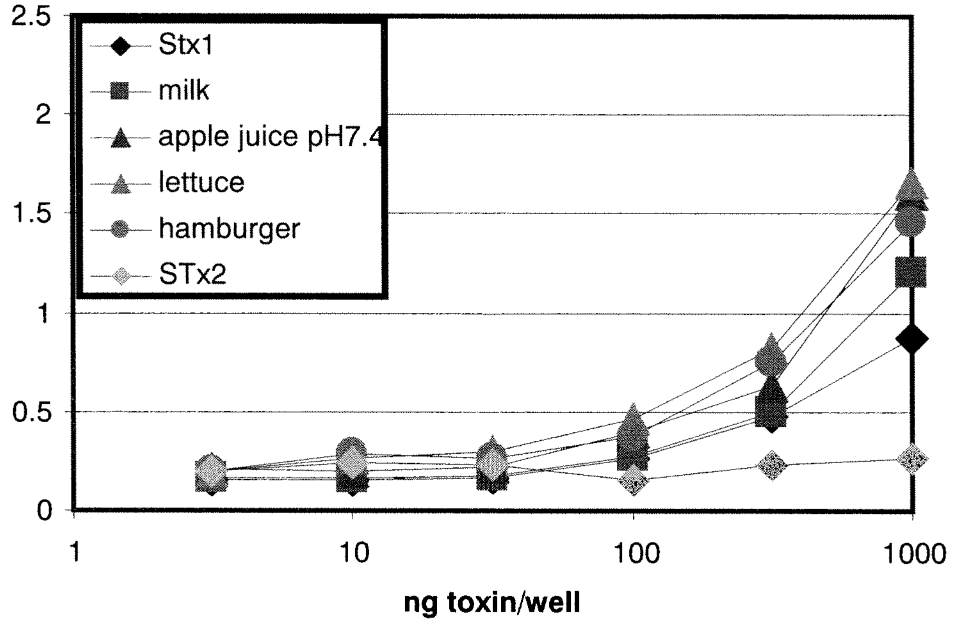
FIG. 10*a* represents a line graph illustrating detection of Shiga toxin 1 or Shiga toxin 2 in food products using one synthetic ligand.
Figure 10B:
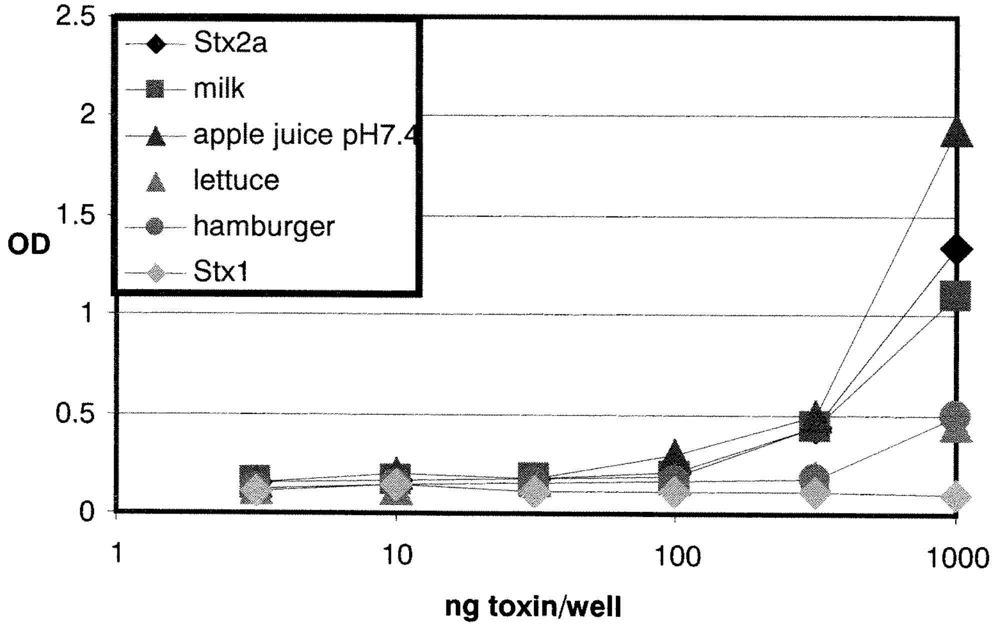
FIG. 10*b* represents a line graph illustrating detection of Shiga toxin 1 or Shiga toxin 2 in food products using another synthetic ligand.
Figure 11A:
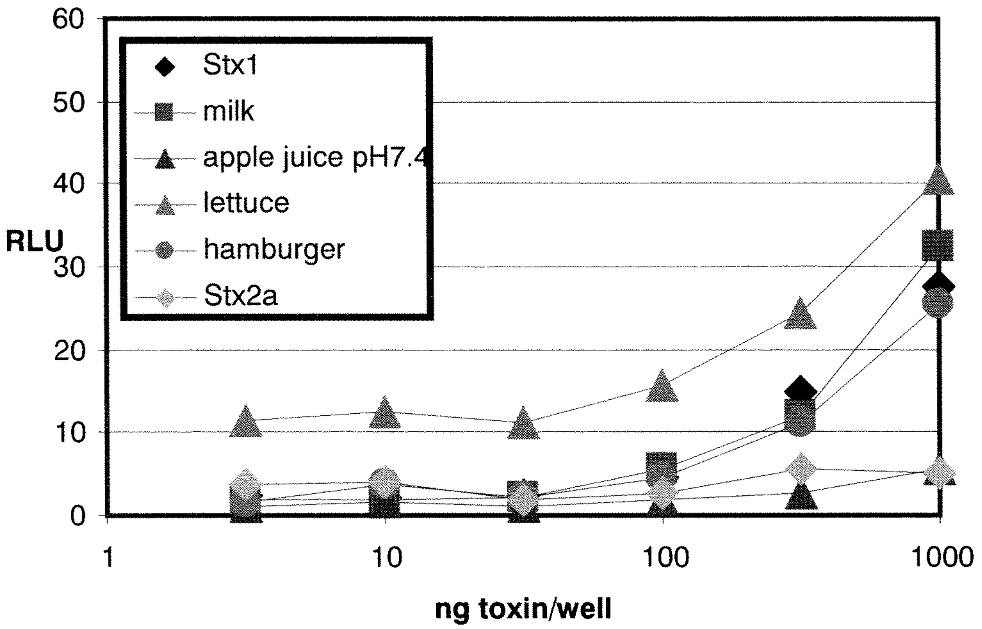
FIG. 11*a* represents a line graph illustrating detection of Shiga toxin 1 or Shiga toxin 2 in food products using one synthetic ligand.
Figure 11B:
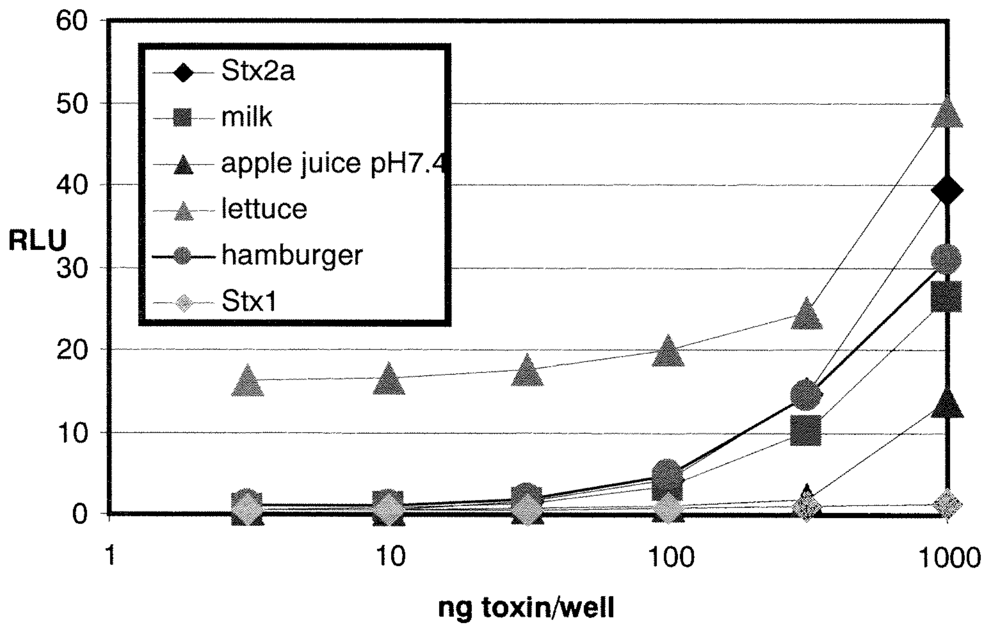
FIG. 11*b* represents a line graph illustrating detection of Shiga toxin 1 or Shiga toxin 2 in food products using another synthetic ligand.

Four basic food products were exposed to both Shiga toxin, 1 (Stx1) and Shiga toxin 2 (Stx2, including Stx2a). Hamburger and lettuce (1 g each) were suspended in 10 mL of PBS, pH 7.4. The lettuce suspension was sonicated three times for 30 seconds each. The hamburger suspension was vortexed for approximately 1 min to suspend solids. The milk and apple juice were used undiluted. In previous studies, low pH was found to influence glycan binding. The pH of the samples was determined. The lettuce, hamburger, and milk had a pH of approximately 7.0. Apple juice was determined to have a pH of 4.0, and was adjusted to pH 7.4 using a small volume of concentrated sodium hydroxide before use. Glycoconjugates (for example, Compound A and B described herein) were coated on strepavidin coated microtiter plates as previously described. Primary rabbit anti-Stx1 and anti-Stx2 (Meridian Biosciences) were used at a 1:1000 dilution. An ELISA assay was utilized, wherein the secondary antibody was goat anti-Rabbit IgG labeled with alkaline phosphotase (used at a 1:3000 dilution) and color was detected with p-nitrophenylphosphate using a plate reader at 405 nm. As noted herein, Compound A substantially binds to Shiga toxin 1 and not Shiga toxin 2, while Compound B substantially binds to Shiga toxin 2 and not Shiga toxin 1. Using an ELISA assay, the Shiga toxin 1 was detected in milk, apple, juice lettuce and hamburger, as illustrated in FIG. 10*a*. Presence of Shiga toxin 2 was detected in all four food products as illustrated in FIG. 10*b*, but detection was reduced in the presence of lettuce and hamburger.

EXAMPLE B

The same food products were tested and prepared as in Example A. However, a luminescent-based assay was used instead where the secondary antibody was goat anti-Rabbit IgG labeled with horseradish peroxidase (used at a 1:10,000 dilution) and the plate was developed by addition of luminol reagent mixed with an oxidizer. Here, both Shiga toxin 1 and Shiga toxin 2 could be detected in the presence of milk and hamburger, but reduced detection was seen in the presence of apple juice for both toxins, and while toxins could be detected in the presence of lettuce, a high background signal was observed (see FIGS. 11*a* and 11*b*).

The foregoing description of embodiments and examples has been presented for purposes of illustration and description. It is not intended to be exhaustive or to limit the invention to the forms described. Numerous modifications are possible in light of the above teachings. Some of those modifications have been discussed, and others will be understood by those skilled in the art. The embodiments as are suited to the particular use contemplated. It is hereby intended that the scope of the invention be defined by the claims appended hereto.

What is claimed is:

1. A method for diagnosing bacterial infections mediated by toxins in a patient comprising obtaining a biological sample from the patient and assaying for the presence of a toxin in a binding assay which uses a compound for detecting said toxins, said compound comprising the general formula (I):

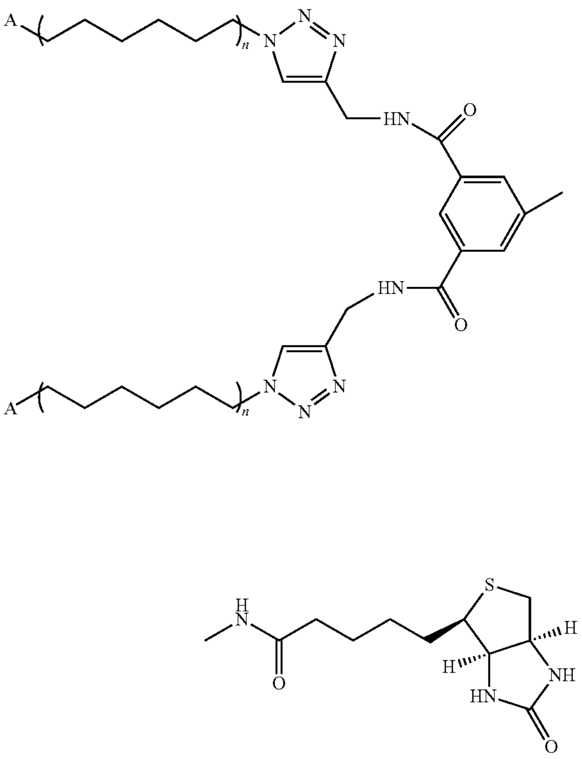

wherein:

n equals 1, 2, 3, 4, 5 or 6, and A comprises a glycoconjugate wherein said glycoconjugate is selected from the group consisting of:

(a)

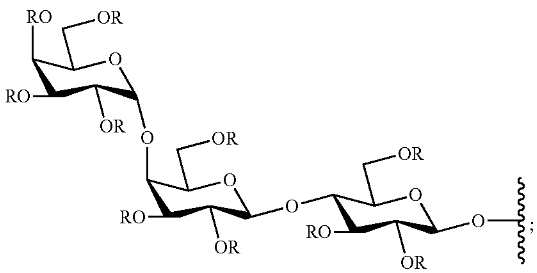

and

-continued (b)

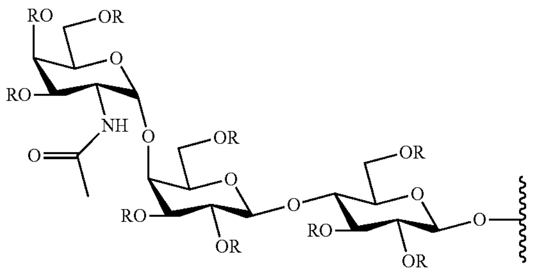

wherein R comprises H; to bind to said toxin;

and wherein said toxin is selected from the group consisting of Shiga toxin 1 and Shiga toxin 2.

2. A method of detecting a Shiga toxin 1 or a Shiga toxin 2 in food, the method comprising:

exposing a food-based sample to a compound for detecting said Shiga toxin, said compound comprising the general formula (I):

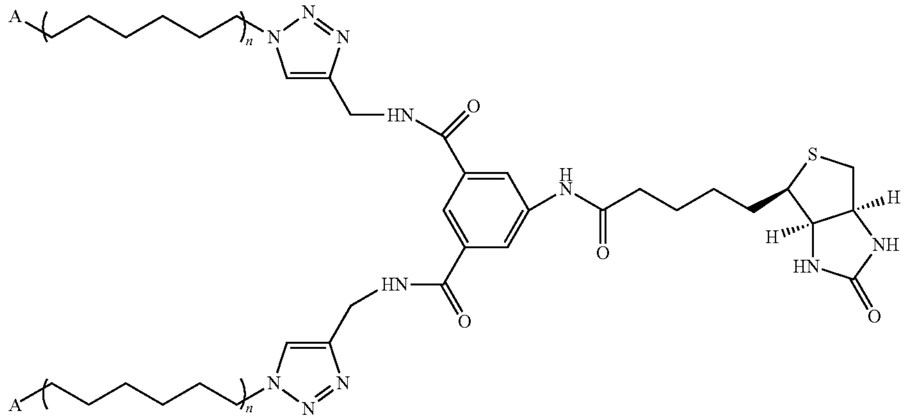

wherein:

n equals 1, 2, 3, 4, 5 or 6, and A comprises a glycoconjugate wherein said glycoconjugate is selected from the group consisting of:

(a)

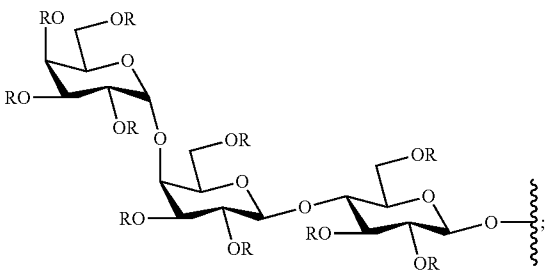

and

-continued (b)

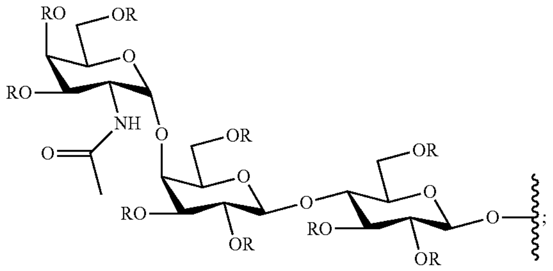

wherein R comprises H; and detecting the presence or absence of said Shiga toxin 1 or said Shiga toxin 2.

3. The method of claim 2, wherein the food-based sample comprises milk, apple juice, lettuce or hamburger.

4. The method of claim 2, wherein the step of detecting the presence or absence of Shiga toxin 1 or Shiga toxin 2 is achieved by using an absorbance based procedure, a luminescence based assay, a fluorescence based assay, a dipstick assay, or by nanoparticles.

5. A biological assay system for detecting the presence of a Shiga toxin 1 or Shiga toxin 2 toxin comprising:

a base layer having a surface;

a capture agent comprising a compound for detecting said Shiga toxin, said compound comprising the general formula (I):

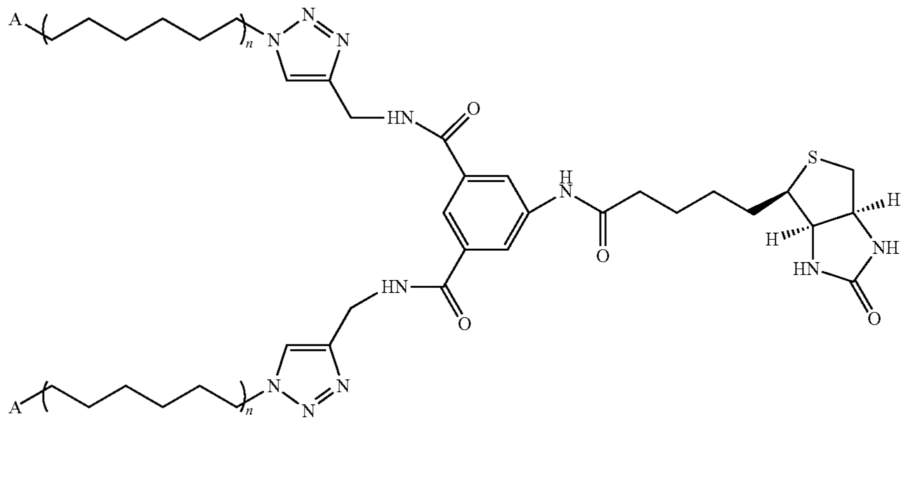

wherein:

n equals 1, 2, 3, 4, 5 or 6, and A comprises a glycoconjugate wherein said glycoconjugate is selected from the group consisting of:

(a)

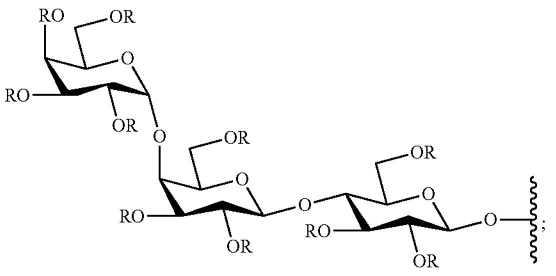

and (b)

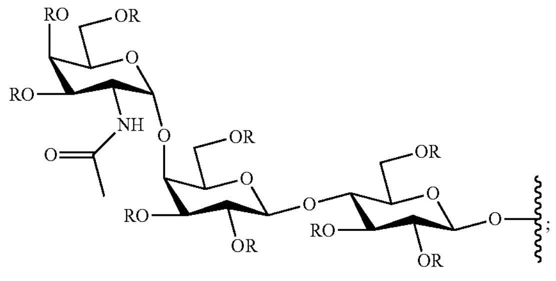

wherein R comprises H; wherein said compound is characterized by its ability to bind to a receptor site of said toxin, wherein said glycoconjugate substantially only binds to Shiga toxin 1 or Shiga toxin 2, the compound being immobilized onto the surface of the base layer; and a detection system configured to measure when the capture agent binds with said toxin.

6. The biological assay system of claim 5, wherein the surface of the base layer has undergone a treatment step to assist in immobilizing the compound.

7. A method to detect the presence or absence of Shiga toxin 1 or Shiga toxin 2, the method comprises:

a) providing a biological assay system having:

i) a base layer having a surface;

ii) a capture agent comprising a compound for detecting said Shiga toxin, said compound comprising the general formula (I):

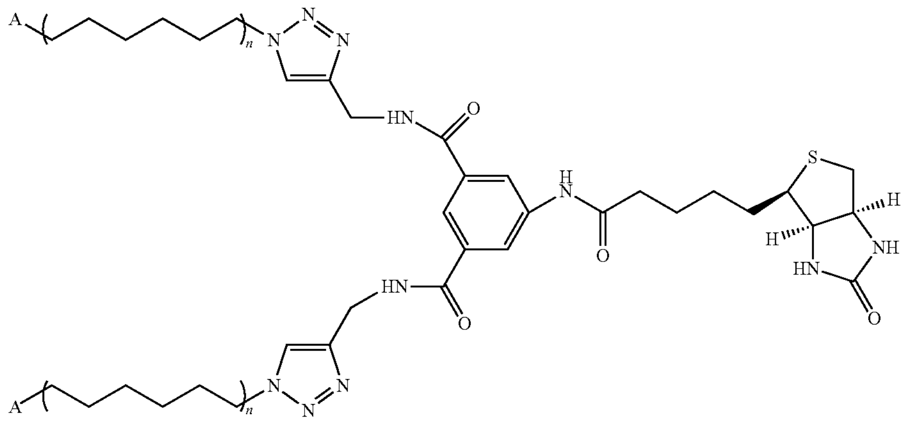

wherein:

n equals 1, 2, 3, 4, 5 or 6, and A comprises a glycoconjugate wherein said glycoconjugate is selected from the group consisting of:

(a)

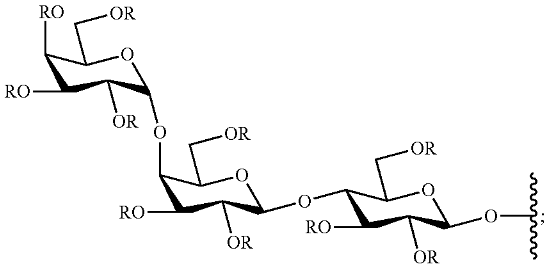

and (b)

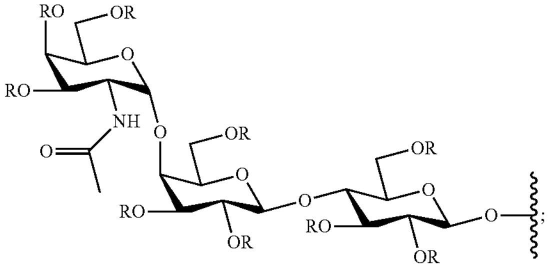

wherein R comprises H; wherein said compound is characterized by its ability to bind to a receptor site of the toxin, the compound being immobilized onto the surface of the film; and iii) a detection system configured to measure when the capture agent binds with the toxin;

b) placing the biological assay system in an environment which may contain the toxin; and c) monitoring the biological assay system for a period of time sufficient to observe an indication to confirm the presence or absence of the toxin.

8. A method for diagnosing bacterial infections mediated by toxins in a patient comprising obtaining a biological sample from said patient and assaying for the presence of a Shiga toxin selected from the group consisting of Shiga toxin 1 or Shiga toxin 2 in a binding assay which uses a compound for detecting said Shiga toxin, said compound comprising the general formula (I):

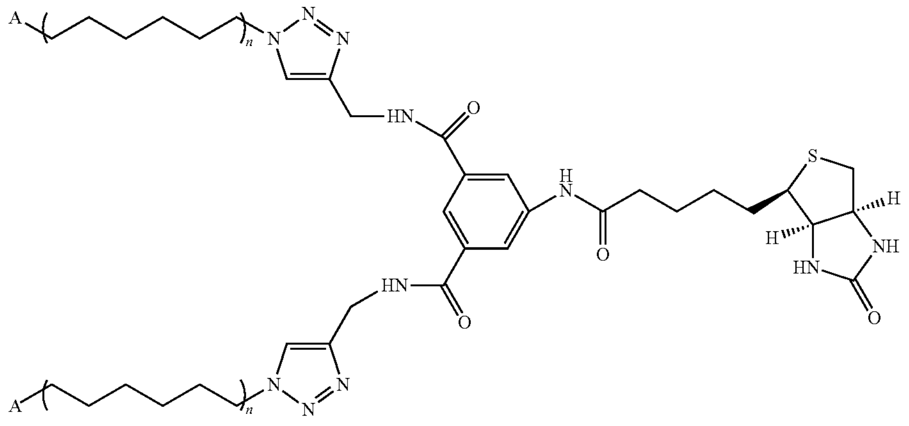

wherein:

n equals 1, 2, 3, 4, 5 or 6, and A comprises a glycoconjugate wherein said glycoconjugate is selected from the group consisting of:

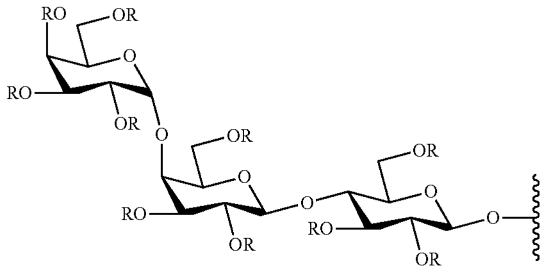

wherein R comprises H and said glycoconjugate substantially only binds Shiga toxin 1 and

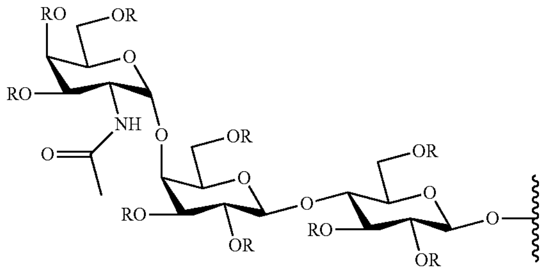

wherein R comprises H, thereof and said glycoconjugate substantially only binds Shiga toxin 2.

9. A method of detecting in food a Shiga toxin selected from the group consisting of Shiga toxin 1 or Shiga toxin 2, the method comprising: exposing a food-based sample to a compound for detecting said Shiga toxin, said compound comprising the general formula (I):

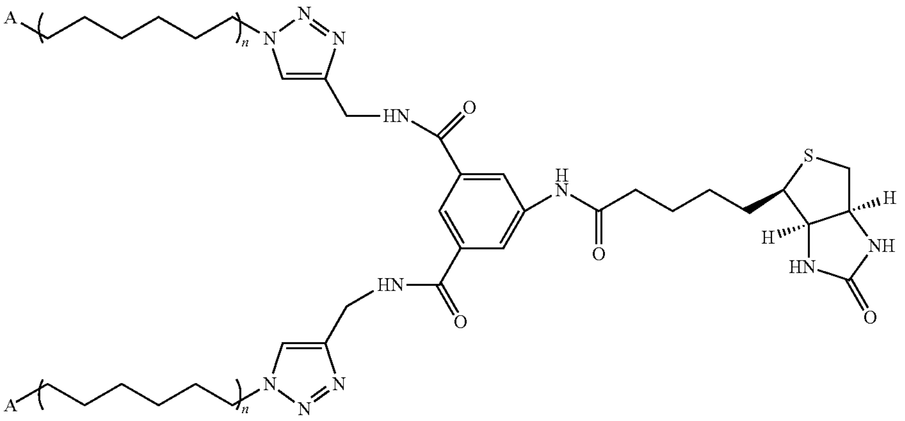

wherein:

n equals 1, 2, 3, 4, 5 or 6, and A comprises a glycoconjugate wherein said glycoconjugate is selected from the group consisting of:

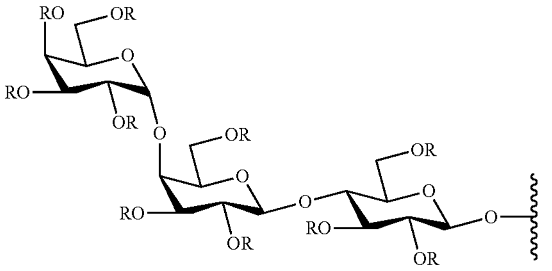

wherein R comprises H thereof and said glycoconjugate substantially only binds Shiga toxin 1 and

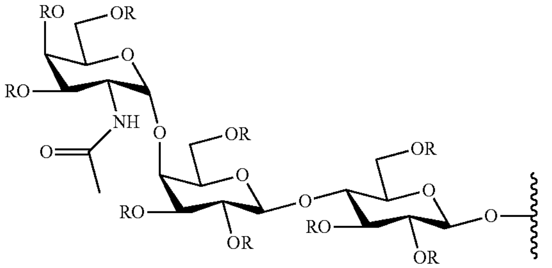

wherein R comprises H and said glycoconjugate substantially only binds Shiga toxin 2; and detecting the presence or absence of said Shiga toxin 1 or said Shiga toxin 2.

10. A method of detecting the presence in a sample of a Shiga toxin selected from the group consisting of Shiga toxin 1 or Shiga toxin 2, said method comprising the steps of:

(a) providing said sample;

(b) exposing said sample to a first compound for detecting said Shiga toxin, said compound comprising the general formula (I):

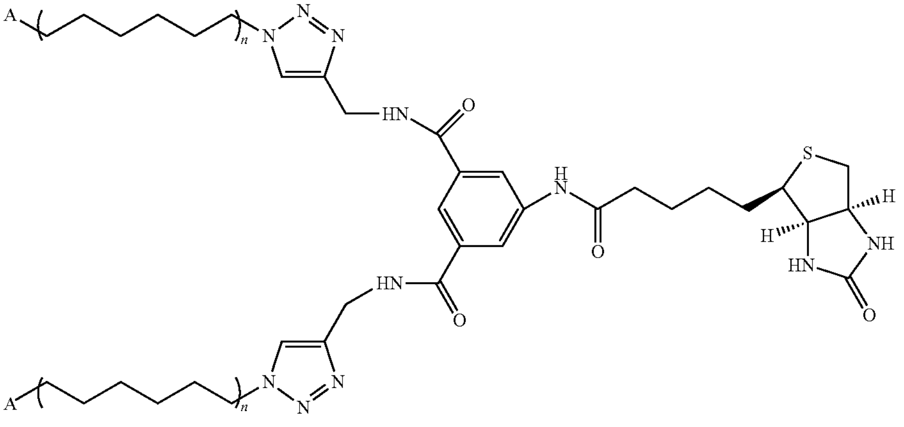

wherein:

n equals 1, 2, 3, 4, 5 or 6, and A comprises a glycoconjugate wherein said glycoconjugate is selected from the group consisting of:

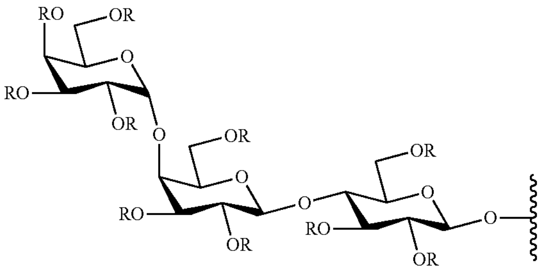

wherein R comprises H and said glycoconjugate substantially only binds Shiga toxin 1 and

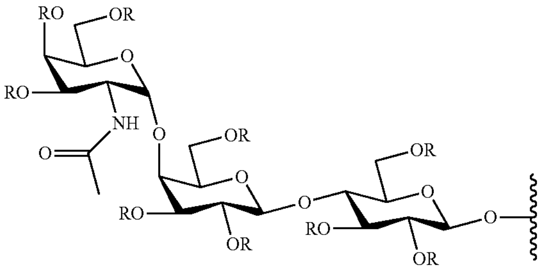

wherein R comprises H and said glycoconjugate substantially only binds Shiga toxin 2; and (c) detecting binding of said first compound.

11. The method of claim 10, further comprising the steps of: exposing said sample to a second compound for detecting said Shiga toxin, comprising the general formula (I):

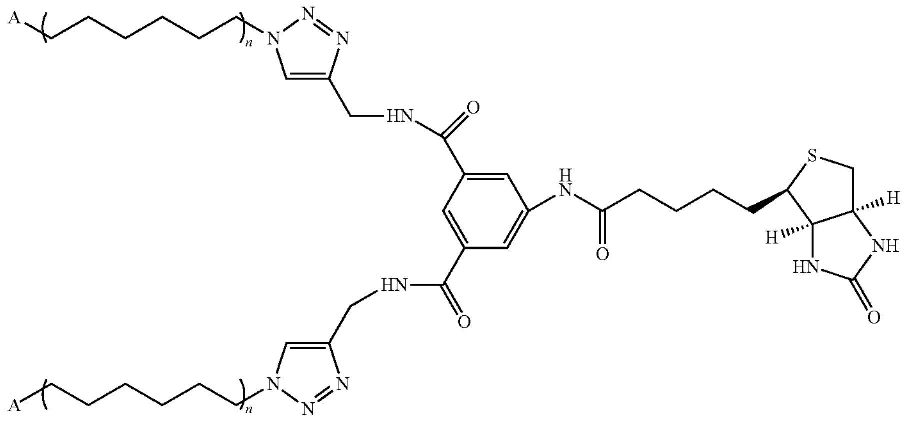

wherein:

n equals 1, 2, 3, 4, 5 or 6, and A comprises a glycoconjugate wherein said glycoconjugate is selected from the group consisting of:

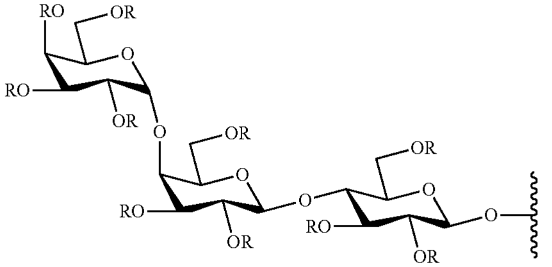

wherein R comprises H and said glycoconjugate substantially only binds Shiga toxin 1 and

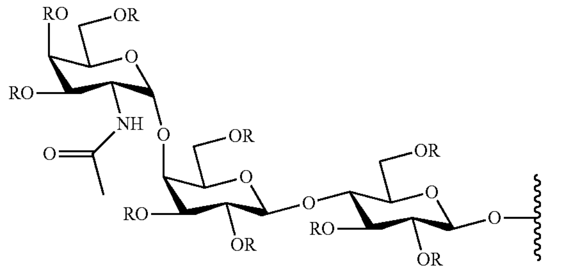

wherein R comprises H and wherein said glycoconjugate substantially only binds Shiga toxin 2; wherein said second compound substantially only binds a second Shiga toxin; and detecting binding of said second compound.

12. A biological assay system for detecting the presence of a Shiga toxin selected from the group consisting of Shiga toxin 1 and Shiga toxin 2, said system comprising: a base layer having a surface;

a capture agent comprising a compound for detecting said Shiga toxin, said compound being immobilized onto said surface of said base layer, said compound comprising the general formula (I):

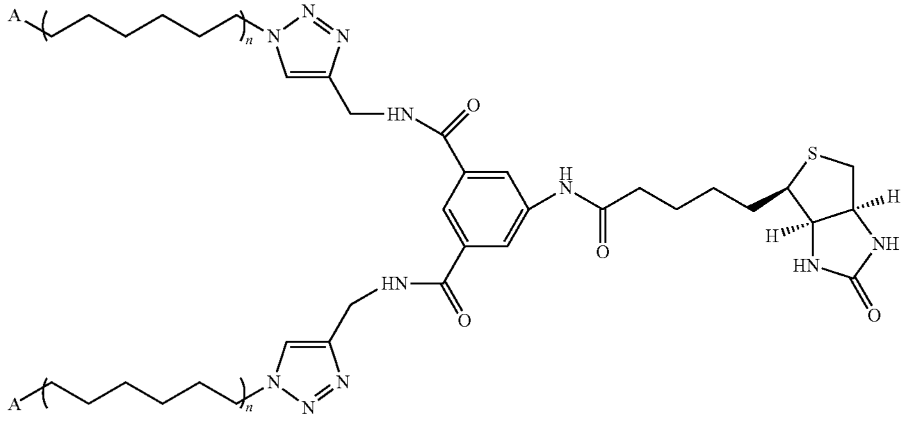

wherein:

n equals 1, 2, 3, 4, 5 or 6, and A comprises a glycoconjugate wherein said glycoconjugate is selected from the group consisting of:

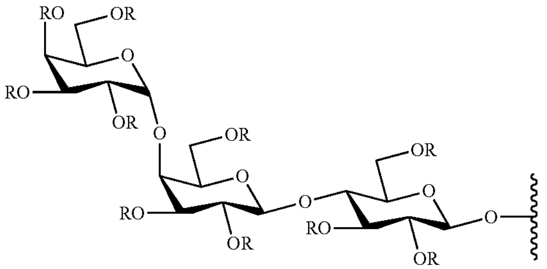

wherein R comprises H and said capture agent substantially only binds Shiga toxin 1 and

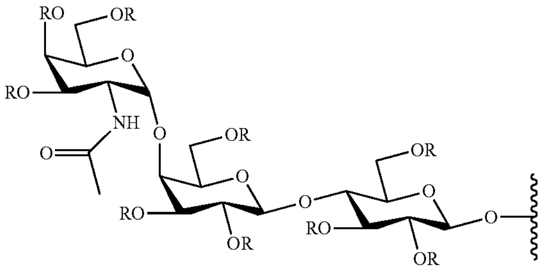

wherein R comprises H and wherein said capture agent substantially only binds Shiga toxin 2; and a detection system configured to measure binding of said capture agent and said toxin.

13. A method to detect the presence of a Shiga toxin selected from the group consisting of Shiga toxin 1 and Shiga toxin 2, said method comprising the steps of:

(a) providing a biological assay system having:

(i) a base layer having a surface:

(ii) a capture agent comprising a compound for detecting said Shiga toxin, said compound comprising the general formula (I):

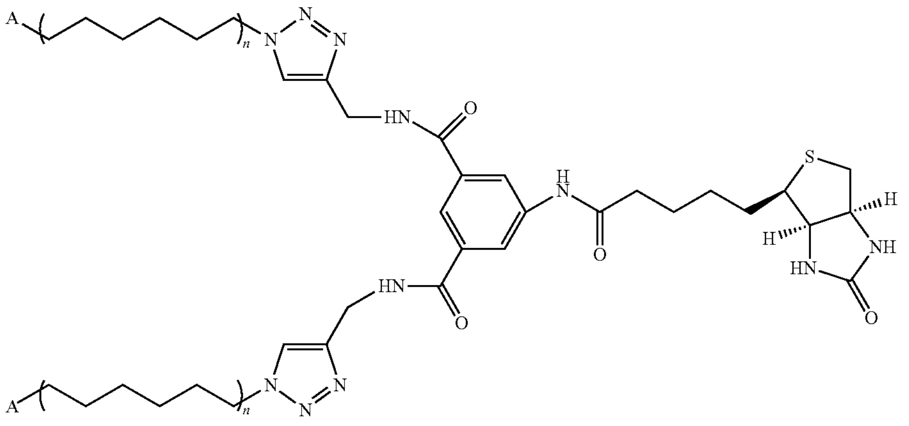

wherein:

n equals 1, 2, 3, 4, 5 or 6, and A comprises a glycoconjugate wherein said glycoconjugate is selected from the group consisting of:

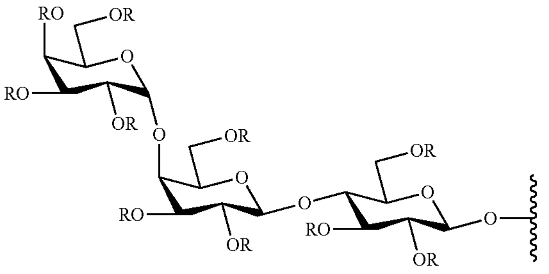

wherein R comprises H and said capture agent substantially only binds Shiga toxin 1 and

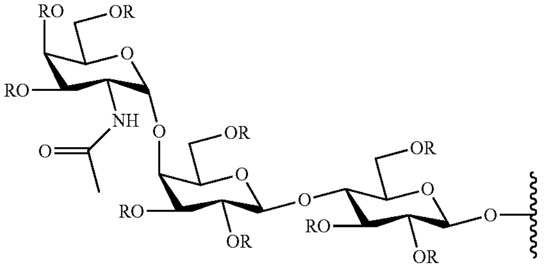

wherein R comprises H and wherein said capture agent substantially only binds Shiga toxin 2; and (iii) a detection system configured to measure binding of said capture agent and said toxin;

(b) placing the biological assay system in an environment which may contain the toxin; and (c) monitoring the biological assay system for a period of time sufficient to observe an indication to confirm the presence or absence of said toxin.

* * * * *

UNITED STATES PATENT AND TRADEMARK OFFICE
CERTIFICATE OF CORRECTION

PATENT NO. : 9,045,516 B2
APPLICATION NO. : 12/104390
DATED : June 2, 2015
INVENTOR(S) : Iyer et al.

It is certified that error appears in the above-identified patent and that said Letters Patent is hereby corrected as shown below:

In the Claims

In Column 22, line 36: please delete the term "thereof".

In Column 14, lines 55-65; Column 15, lines 55-65, Column 17, lines 35-45; Column 19, lines 35-45; Column 21, lines 30-40; Column 23, lines 5-15; Column 24, lines 5-15; Column 25, lines 27-37; Column 27, lines 7-17; and Column 28, lines 9-19: the formula should appear as:

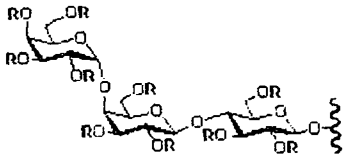

In Column 15, lines 1-12; Column 16, lines 5-15; Column 17, lines 55-65; Column 19, lines 55-65; Column 22, lines 24-34; Column 23, lines 23-33; Column 24, lines 25-35; Column 26, lines 20-23, Column 27, lines 24-34; Column 28, lines 25-35: the formula should appear as:

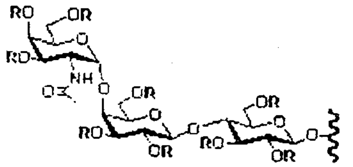

Signed and Sealed this
Eighth Day of September, 2015

Michelle K. Lee
*Director of the United States Patent and Trademark Office*